(12) United States Patent
Zhang et al.

(10) Patent No.: US 11,970,529 B2
(45) Date of Patent: Apr. 30, 2024

(54) PROTEIN BINDING TO FIBRONECTIN B DOMAIN

(71) Applicant: HEFEI LIFEON PHARMACEUTICAL CO., LTD., Hefei (CN)

(72) Inventors: Mei Zhang, Hefei (CN); Junqiu Ji, Hefei (CN); Meihua Gao, Hefei (CN); Jun Chen, Hefei (CN)

(73) Assignee: Hefei Lifeon Pharmaceutical Co., Ltd., Hefei (CN)

( * ) Notice: Subject to any disclaimer, the term of this patent is extended or adjusted under 35 U.S.C. 154(b) by 118 days.

(21) Appl. No.: 17/520,480

(22) Filed: Nov. 5, 2021

(65) Prior Publication Data

US 2022/0089709 A1 Mar. 24, 2022

Related U.S. Application Data

(63) Continuation of application No. 16/652,384, filed as application No. PCT/CN2018/108532 on Sep. 29, 2018, now Pat. No. 11,192,943.

(30) Foreign Application Priority Data

Sep. 30, 2017 (CN) .......................... 201710918370.7

(51) Int. Cl.
| | |
|---|---|
| C07K 16/00 | (2006.01) |
| A61K 39/395 | (2006.01) |
| A61P 35/00 | (2006.01) |
| C07K 14/47 | (2006.01) |
| C07K 16/18 | (2006.01) |
| C07K 16/46 | (2006.01) |
| G01N 33/53 | (2006.01) |
| A61K 39/00 | (2006.01) |

(52) U.S. Cl.
CPC .............. C07K 16/18 (2013.01); A61P 35/00 (2018.01); C07K 14/47 (2013.01); *A61K 2039/505* (2013.01); *C07K 2317/21* (2013.01); *C07K 2317/34* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,703,143 B2 | 4/2014 | Neri et al. | |
| 9,696,320 B2 | 7/2017 | Narimatsu et al. | |
| 2003/0176663 A1 | 9/2003 | Neri et al. | |
| 2003/0220239 A1* | 11/2003 | Simard | A61P 35/00 424/139.1 |
| 2006/0133994 A1* | 6/2006 | Neri | C07K 16/18 424/1.49 |
| 2016/0200789 A1 | 7/2016 | Hemmerle et al. | |
| 2019/0002516 A1 | 1/2019 | Zhang et al. | |
| 2019/0185550 A1 | 6/2019 | Ji et al. | |
| 2020/0283511 A1 | 3/2020 | Zhang et al. | |

FOREIGN PATENT DOCUMENTS

| | | |
|---|---|---|
| CA | 2421783 | 3/2002 |
| CA | 2628552 | 5/2017 |
| CN | 1219968 A | 6/1999 |
| CN | 104395342 | 3/2015 |
| WO | WO 97/45544 | 12/1997 |
| WO | WO 99/58570 | 11/1999 |
| WO | WO 01/62800 | 8/2001 |
| WO | WO 02/20563 | 3/2002 |
| WO | WO 03/076469 | 9/2003 |
| WO | WO 2007/054120 | 5/2007 |

OTHER PUBLICATIONS

Extended European Search Report for European Patent Application No. 18861266.7, dated Dec. 14, 2021 (8 pages).
Zang et al., "Antibody Specificity for Extra Domain B of Fibronectin Demonstrates Elevated Levels of Both Extra Domain B(+) and B(−) Fibronectin in Osteoarthritic Canine," *Matrix Biology* 14:623-633, 1995.
Klimka et al., "Human Anti-CD30 Recombinant Antibodies by Guided Phage Antibody Selection using Cell Panning," *Br. J. Cancer*, vol. 83:252-260, 2000.
Menrad et al., "ED-B Fibronectin as a Target for Antibody-Based Cancer Treatments," *Expert. Opin. Ther. Targets*, vol. 9:491-500, 2005.
Ventura et al., "C6: A Monoclonal Antibody Specific for a Fibronectin Epitope Situated at the Interface between the Oncofoetal Extra-Domain B and the Repeat III8," *PLoS ONE*: vol. 11e0148103, 2016.
International Search Report for PCT/CN2018/108532, dated Jan. 7, 2019 (6 pages).

* cited by examiner

*Primary Examiner* — Maher M Haddad
(74) *Attorney, Agent, or Firm* — Klarquist Sparkman, LLP

(57) ABSTRACT

The present invention relates to an epitope on fibronectin B (ED-B) domain, more specifically to an antibody or an antibody fragment of ED-B domain, and can be widely applied in in-vitro detection and in-vivo positioning of ED-B domain as well as in targeted cancer therapy.

12 Claims, 5 Drawing Sheets
Specification includes a Sequence Listing.

FIG. 1

*Heavy-chain variable region*

```
1           10         20         30              CDR 1
EVQLLESGGGLVQPGGSLRLSCAASGFTFS                   SYAMS   WVRQAPGKGLEWVS
                                                          40
       50         60         70         80                CDR 2
                                                          RISPSGSSTYYADSVKG
                                                          90
RFTISRDNSKNTLYLQMNSLRAEDTAVYYCAR       RMSYFDY    WGQGTLVTVSS
                                       CDR 3                  110
                                       100
```

*Linker*

```
1          10
GGGGSGGGGSGGGGSS
```

*Light-chain variable region*

```
1          10         20                CDR 1
QSALTQPASVSGSPGQSITISC          SGDSLGIFRSGMVS          WYQQHPGKAPKLMIY
                                30                      40
                                                                    50
       60         70         80         90             CDR 3
GVSNRFSGSKSGNTASLTISGLQAEDEADYYC        QSWDGRQP       VFGGGTKLTVLG
                                                        100        110
                                        CDR 2
                                        LPTSRPS
```

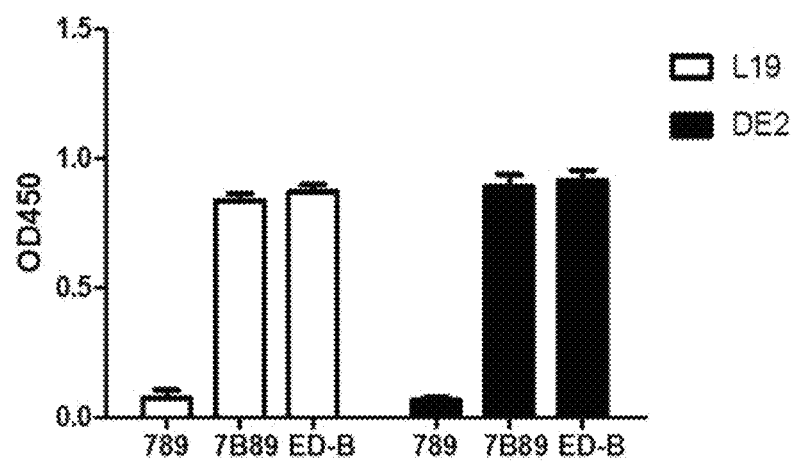
FIG. 2
FIG. 3A
FIG. 3B
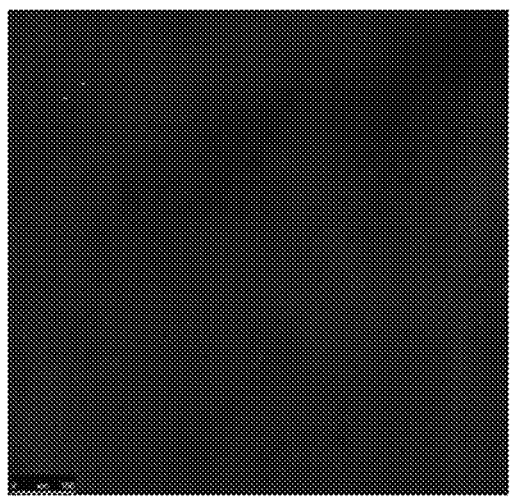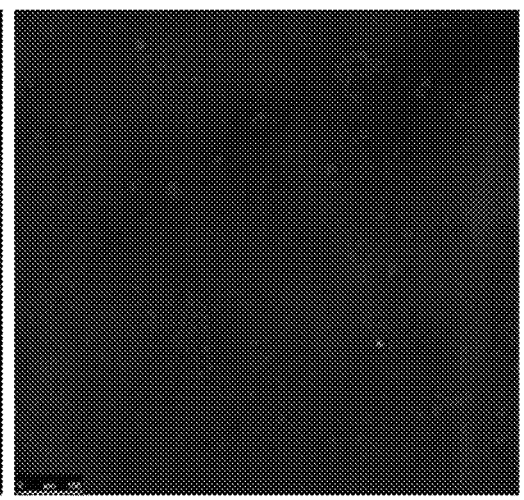

SEQ ID NO: 16:

```
1         10        20        30
EVPQLTDLSFVDITDSSIGLRWTPLNSSTIIGYRITV
        40        50        60        70
VAAGEGIPIFEDFVDSSVGYYTVTGLEPGIDYDISVI
          80        90
TLINGGESAPTTLTQQT
```

PROTEIN BINDING TO FIBRONECTIN B DOMAIN

CROSS REFERENCE TO RELATED APPLICATIONS

This application is a continuation of U.S. application Ser. No. 16/652,384, filed Mar. 30, 2020, issued as U.S. Pat. No. 11,192,943 on Dec. 7, 2021, which is the U.S. National Stage of International Application No. PCT/CN2018/108532, filed Sep. 29, 2018, which claims the benefit of China Application No. 201710918370.7, filed Sep. 30, 2017. The above-listed applications are herein incorporated by reference in their entirety.

INCORPORATION OF ELECTRONIC SEQUENCE LISTING

The Sequence Listing is submitted as an ASCII text file, created on Nov. 2, 2021, 44.4 KB, which is incorporated by reference herein.

TECHNICAL FIELD

The present invention relates to a novel epitope of fibronectin B domain, and an antibody, especially a monoclonal antibody or an antibody fragment, specifically binding to the epitope, having a biological activity of recognizing tumor or inhibiting tumor growth, or of killing tumor cells. In addition, the present invention also relates to a method of preparing the antibody and a pharmaceutical composition comprising the antibody.

BACKGROUND OF THE INVENTION

Chemotherapy and radiotherapy are commonly-used tumor treatments, which result in remarkable toxic and side effects on normal tissues due to low specificity. Physiological functions of normal organs are affected while cancer cells are killed, and the immunity and the life quality of patients are reduced. One way to improve the specificity of a tumor therapeutic agent is to target the agent to tumor cells by means of an antibody or an antibody fragment capable of recognizing a tumor cell marker, resulting in targeted killing of the tumor. First, one needs to find a tumor marker that can be expressed on the outer surface of the cell membrane, i.e. a protein that is expressed only on the surface or in the extracellular matrix of tumor cells but in a very small amount or even not expressed in normal cells or tissues.

Fibronectin (FN) is a multifunctional glycoprotein, widely found in the extracellular matrix, plasma and other body fluids, expressed by epithelial cells, endothelial cells, fibroblasts, hepatocytes and so on, and involved in the cell adhesion, deformation and distribution, as well as the formation of blood vessels.

The FN gene is about 75 kb in length, including about 50 exons, and mainly composed of three types of homologous repeat units, type I, II and III. Domain B is a complete repeat of 91 amino acids in the type III repeat sequence of FN encoded by a single exon. During the expression of the FN gene, there are two cases, the FN(B+) including the B domain and the other FN(B−) not including the B domain, and both are considered to play an important role in the development of the individual. The FN(B+) is rarely expressed in normal tissues of an adult, but is highly expressed again during a trauma, disease, wound healing, especially tumor growth, e.g. the FN(B+) containing the B domain is highly expressed in cells such as gastric cancer, colorectal cancer, lung cancer, breast cancer cells and the like. The FN(B+) is a marker protein of tumor tissues, as it is not expressed in normal tissues of an adult but is highly expressed in blood vessels of various tumor tissues as shown by in-vitro immunohistochemistry assay and in-vivo targeting localization. Thus, the B domain of FN is also referred as an Extra-domain B (ED-B).

A targeting antibody developed on the basis of the ED-B domain can be used for targeting a candidate drug such as a cytotoxin and so on to a tumor site and effectively inhibit or kill tumor cells, thereby achieving the purpose of treatment while reducing damage to normal tissues and reducing toxic side effects.

It is trend that a therapeutic antibody is developed to a fully human antibody, which is clinically advantageous over a murine antibody, such as low immunogenicity, longer in vivo half-life of antibody and mediating immunoregulation, ADCC and CDC effects by virtue of human immunoglobulin Fc segment, thereby enhancing the biological effects of antibody.

Since the amino acid sequence of the human ED-B is 100% homologous to that of the mouse ED-B, it is difficult for the mouse immune system to immunoreact with the human ED-B domain to produce an anti-ED-B antibody, e.g. the mouse monoclonal antibody BC-1 obtained by hybridoma technology (Carnemolla, Leprini et al. J Biol Chem 1992, 24689-24692) cannot recognize the ED-B domain directly, but indirectly specifically binds to the FN of ED-B positive by recognizing an antigenic epitope in a domain adjacent to the ED-B. Now, with the aid of genetic engineering technologies, an artificially synthesized antibody gene is directly expressed utilizing phage display technology, and an antibody with particular functions is obtained through panning, without need of an immune system of a higher animal body. Therefore, there provides a technology for developing a fully human-origin recombinant antibody. Currently, the ED-B human antibodies with high specificity such as CGS-1, CGS-2, L19 (Carnemolla, Neri et al. Int J Cancer 1996, 397-405, Pini, Viti et al. J Biol Chem 1998, 21769-21776) and B5 (Ji J, Zhang M, Gao M, et al. HUMAN ANTIBODY AGAINST ED-B DOMAIN OF FIBRONECTIN AND USES THEREOF. WO2014194784A1) have been reported. The CGS-1, CGS-2 and L19 have an affinity of $5.4 \times 10^{-8}$M, $1.1 \times 10^{-9}$M and $8.7 \times 10^{-10}$M respectively as measured by BIAcore assay. In particular, the clinical research of the antibody L19 sufficiently proved that a specific antibody drug developed against the antigen ED-B has a remarkable tumor inhibiting or killing effect.

SUMMARY OF THE INVENTION

In one aspect, the invention provides a novel linear epitope of ED-B domain, consisting of an amino acid sequence selected from the group consisting of VDITDS (SEQ ID NO: 76), TGLEPGIDY (SEQ ID NO: 88) and NSSTIIGYR (SEQ ID NO: 81).

In one aspect, the invention provides an isolated antibody or antigen-binding fragment thereof that specifically binds to an epitope selected from the group consisting of VDITDS (SEQ ID NO: 76), TGLEPGIDY (SEQ ID NO: 88) and NSSTIIGYR (SEQ ID NO: 81).

In an embodiment, the invention provides an isolated antibody or antigen-binding fragment thereof, wherein the antibody or antigen-binding fragment thereof comprises three heavy chain complementarity determining regions (HCDR) and three light chain complementarity determining regions (LCDR), wherein the HCDR1, HCDR2 and HCDR3 comprise the amino acid sequences as set forth in SEQ ID NO: 5, SEQ ID NO: 6 and SEQ ID NO: 7 respectively, and the LCDR1 comprises an amino acid sequence selected from the group consisting of SEQ ID NOs: 8, 95-118 and 143, the LCDR2 comprises an amino acid sequence selected from the group consisting of SEQ ID NOs: 9, 119-142 and 144, and the LCDR3 comprises an amino acid sequence as set forth in SEQ ID NO: 10.

In an embodiment, an isolated antibody or antigen-binding fragment thereof according to the invention comprises a heavy chain variable region (VH) comprising an amino acid sequence as set forth in SEQ ID NO: 1. In an embodiment, an antibody or antigen-binding fragment thereof according to the invention comprises a light chain variable region (VL) comprising an amino acid sequence as set forth in SEQ ID NO: 3 or 145 or an amino acid sequence having at least 95%, 96%, 97%, 98% or 99% identity thereto.

In an embodiment, an antibody according to the invention comprises an amino acid sequence as set forth in SEQ ID NO: 13, SEQ ID NO: 14, SEQ ID NO: 146, amino acids 1-241 of SEQ ID NO: 13, or amino acids 1-242 of SEQ ID NO: 13.

In one aspect, the invention provides a pharmaceutical composition comprising an isolated antibody or antigen-binding fragment thereof according to the invention, optionally further comprising a fusion protein, a radioisotope, a chemical drug and/or a nanoparticle.

In one aspect, the invention provides use of an isolated antibody or antigen-binding fragment thereof or a pharmaceutical composition comprising the same according to the invention in the manufacture of a medicament for the prevention, diagnosis and treatment of cancer.

In an embodiment, the cancer is a cancer expressing FN(B+) containing ED-B domain, e.g., selected from the group consisting of nasopharyngeal carcinoma, head and neck cancer, esophageal cancer, gastric cancer, colorectal cancer, lung cancer, breast cancer and soft tissue sarcoma.

In one aspect, the invention provides a kit comprising an isolated antibody or antigen-binding fragment thereof according to the invention, which can be used for (i) diagnosing an in vivo distribution or a pathological tissue section of tumor tissue, (ii) analyzing and characterizing a cell or a protein, or (iii) affinity purifying a cell or a protein molecule comprising an ED-B protein domain.

In one aspect, the invention provides use of an isolated antibody or antigen-binding fragment thereof according to the invention in the manufacture of a kit for (i) diagnosing an in vivo distribution or a pathological tissue section of tumor tissue, (ii) assaying and characterizing a cell or a protein, or (iii) affinity purifying a cell or a protein molecule comprising an ED-B protein domain.

In one aspect, the invention provides a polynucleotide molecule encoding an isolated antibody or antigen-binding fragment thereof according to the invention.

BRIEF DESCRIPTION OF THE DRAWINGS

FIG. 1 shows the heavy and light chain variable region amino acid sequences of the DE2 antibody, wherein the underlined amino acids are CDR regions, the double-underlined amino acids are random sequences in the antibody repertoire, and the three-underlined amino acids are random sequences in the A11 antibody repertoire.

FIG. 2 verifies that the DE2 antibody specifically recognizes an antigenic ED-B domain by ELISA experiments.

FIGS. 3A-3B verify that the DE2 antibody specifically recognizes FN(B+) cells by cellular immunofluorescence experiments. FIG. 3A is a negative control, wherein the cells are CHO-789 cells that do not express ED-B, and the cells of FIG. 3B are CHO-7B89 cells that express ED-B. The antibody is the FITC-labeled DE2 antibody.

CONTENTS OF THE INVENTION

Figure 4:
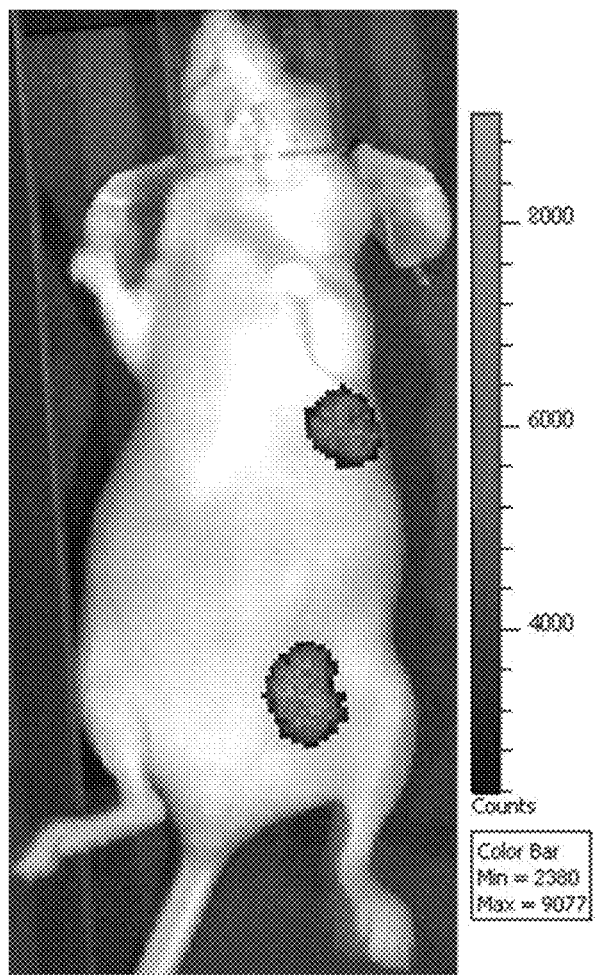
FIG. 4 shows the distribution of DE2 antibody in tumor-bearing mice. The Cy5.5 labeled DE2 antibody can be specifically distributed in an ED-B high-expressing implanted tumor tissue by the living body fluorescence imaging method for a small animal, and the antibody distribution is difficult to be detected in other tissues.

The inventors, using antibody gene synthesis and phage display technology, have discovered a specific single-chain antibody which directly recognizes an ED-B domain alone or fibronectin containing ED-B domain FN(B+), as well as a fusion protein of other protein(s) and an ED-B domain. The affinity of the obtained candidate antibody is 16 times of that of the L19 antibody by an ELISA assay. The affinity of the obtained antibody is 9 times of that of the L19 by BIAcore assay. The antibody is expected to have a higher affinity and better targeting effect on the antigen ED-B. The obtained antibody's light chain has an amino acid sequence of human Lambda chain, which is different from the amino acid sequence of human Kappa chain of the L19, and diversifies the types of antibody against ED-B.

The obtained antibody can be used in the development of an antitumor drug, such as radioisotope labeling of antibody, fusion with a cytotoxin, coupling with a chemical drug, coupling with a nanoparticle and the like. A drug can be highly enriched in a tumor tissue highly expressing FN(B+) to specifically kill tumor cells in a targeted manner by virtue of the targeting effect of the obtained antibody, so that the drug effect can be improved with less damage to normal tissues. The structure of the obtained single-chain antibody can miniaturize the antibody drug, improve the permeability of the antibody in a human body, get into the inside of a tumor tissue along tumor blood vessels and exert better tumor killing effects; moreover, the single-chain antibody can be flexibly changed into various forms of antibody, such as a natural antibody structure, a minibody, a dibody, a multi-antibody fusion form and the like. The stability, permeability, application and the like of the antibody can be changed through modification of the antibody structure. In addition, the obtained antibody can be developed into a tumor diagnostic agent for detecting the tumor tissue in vivo and in vitro, or for development of other various immune-related reagents.

The inventors have found that there are two regions in the ED-B domain of fibronectin that bind to an antibody with very high affinity, located in an irregular coiled region of the ED-B domain. It can be found through further analysis that an antigenic epitope of ED-B recognized by a high affinity ED-B antibody consists of an ED-B polypeptide fragment selected from the group consisting of: VDITDS (SEQ ID NO: 76), TGLEPGIDY (SEQ ID NO: 88) and NSSTIIGYR (SEQ ID NO: 81).

The inventors have obtained a recombinant anti-human ED-B protein domain monoclonal antibody or an antibody fragment, wherein the antibody fragment is preferably an antigen-binding fragment, and the antibody or the antibody fragment can be effectively bind to fibronectin (FN) containing ED-B domain (abbreviated as FN(B+)) and can be used for the detection and diagnosis of the FN(B+) as well as for targeted therapy of FN(B+)-high-expressing tumors, or can be used in a combined treatment with other antineoplastic agents.

Accordingly, the invention provides an isolated antibody or an antibody fragment that specifically recognizes and binds the ED-B domain of human fibronectin (FN). In a particular embodiment, the invention provides an antibody or an antibody fragment that specifically recognizes and/or binds to a linear epitope consisting of an ED-B polypeptide fragment selected from the group consisting of: VDITDS (SEQ ID NO: 76), TGLEPGIDY (SEQ ID NO: 88) and NSSTIIGYR (SEQ ID NO: 81).

In a particular embodiment, an antibody or antibody fragment according to the invention comprises an amino acid sequence of the heavy chain variable region CDR3 comprising the amino acid sequence RMSYFDY (SEQ ID NO: 7).

In another particular embodiment, an antibody or antibody fragment according to the invention comprises an amino acid sequence of the light chain variable region CDR3 comprising the amino acid sequence QSWDGRQP (SEQ ID NO: 10).

In another particular embodiment, an antibody or antibody fragment according to the invention comprises a heavy chain variable region CDR3 having the amino acid sequence RMSYFDY (SEQ ID NO: 7) and a light chain variable region CDR3 having the amino acid sequence QSWDGRQP (SEQ ID NO: 10).

In another particular embodiment, an antibody or antibody fragment according to the invention comprises three heavy chain variable region CDRs having the amino acid sequences SYAMS (SEQ ID NO: 5), RISPSGSSTYYADSVKG (SEQ ID NO: 6), and RMSYFDY (SEQ ID NO: 7), respectively.

In a particular embodiment, an antibody or antibody fragment according to the invention comprises a light chain CDR1 comprising an amino acid sequence selected from the group consisting of SEQ ID NOs: 8, 95-118 and 143.

In a particular embodiment, an antibody or antibody fragment according to the invention comprises a light chain CDR2 comprising an amino acid sequence selected from the group consisting of SEQ ID NOs: 9, 119-142 and 144.

In another particular embodiment, an antibody or antibody fragment according to the invention comprises three light chain variable region CDRs, each having an amino acid sequence of:
LCDR1: the amino acid sequence selected from the group consisting of SEQ ID NOs: 8, 95-118 and 143, e.g. SEQ ID NO: 8, 95, 97, 99, 100, 114 or 143,
LCDR2: the amino acid sequence selected from the group consisting of SEQ ID NOs: 9, 119-142 and 144, e.g., SEQ ID NO: 9, 119, 121, 123, 124, 138 or 144, and
LCDR3: SEQ ID NO: 10.

In another particular embodiment, an antibody or antibody fragment according to the invention comprises three heavy chain variable region CDRs and three light chain variable region CDRs, wherein the amino acid sequences of the three heavy chain variable region CDRs consist of SYAMS (SEQ ID NO: 5), RISPSGSSTYYADSVKG (SEQ ID NO: 6) and RMSYFDY (SEQ ID NO: 7), respectively, and the amino acid sequences of the three light chain variable region CDRs consist of SGDSLGIFRSGMVS (SEQ ID NO: 8), LPTSRPS (SEQ ID NO: 9) and QSWDGRQP (SEQ ID NO: 10), respectively.

In another particular embodiment, the invention provides an isolated antibody or antigen-binding fragment thereof that specifically recognizes and binds the ED-B domain of human fibronectin (FN), wherein the antibody or antigen-binding fragment thereof comprises a light chain variable region (VL) and a heavy chain variable region (VH), the heavy chain variable region comprising:
a VH CDR1 comprising an amino acid sequence as set forth in SEQ ID NO: 5,
a VH CDR2 comprising an amino acid sequence as set forth in SEQ ID NO: 6, and
a VH CDR3 comprising an amino acid sequence as set forth in SEQ ID NO: 7,
the light chain variable region comprising:
a VL CDR1 comprising an amino acid sequence as set forth in SEQ NO: 8 or 143,
a VL CDR2 comprising an amino acid sequence as set forth in SEQ ID NO: 9 or 144, and
a VL CDR3 comprising an amino acid sequence as set forth in SEQ ID NO: 10.

An "isolated antibody" means that the antibody (1) is not associated with a naturally associated component that accompanies it in its natural state, (2) does not contain other proteins from the same species, (3) is expressed by cells from different species, or (4) does not occur in nature. Thus, a chemically synthesized polypeptide or a polypeptide synthesized in a cell system other than a cell from which the polypeptide is naturally derived will be "isolated" from its naturally associated components. The protein may also be substantially free of naturally associated components by isolation, i.e., using protein purification techniques well-known in the art.

As used herein, an "antibody" refers to an immunoglobulin and an immunoglobulin fragment, regardless of natural or partially or fully synthetically (e.g., recombinantly) produced, including any fragment thereof that comprises at least partial variable region of an immunoglobulin molecule and retains the binding specificity of the full-length immunoglobulin. Thus, an antibody includes any protein having a binding domain that is homologous or substantially homologous to the antigen binding domain (antibody binding site) of an immunoglobulin. Antibody includes synthetic antibodies, recombinantly produced antibodies, multispecific antibodies (e.g., bispecific antibodies), human antibodies, non-human antibodies, humanized antibodies, chimeric antibodies, intracellular antibodies, and antibody fragments, e.g., but not limited to, Fab fragments, Fab' fragments, F(ab')$_2$ fragments, Fv fragments, disulfide bridge-linked Fv (dsFv), Fd fragments, Fd' fragments, single-chain Fvs (scFvs), single-chain Fabs (scFabs), diabodies, or antigen-binding fragments of any of the foregoing antibodies. The antibody provided herein comprises a member of any immunoglobulin types (e.g., IgG, IgM, IgD, IgE, IgA, and IgY), any class (e.g., IgG1, IgG2, IgG3, IgG4, IgA1 and IgA2), or subclass (e.g., IgG2a and IgG2b).

As used herein, the "antibody fragment" or "antigen-binding fragment" of an antibody refers to any portion of a full-length antibody that is less than full-length, but comprises at least a portion of the variable region (e.g., one or more CDRs and/or one or more antibody binding sites) of the antibody that binds an antigen, and thus retains the binding specificity as well as at least partial specific binding capacity of the full-length antibody. Thus, an antigen-binding fragment comprises an antigen-binding portion that binds the same antigen as the antibody from which the antibody fragment is derived. Antibody fragment includes antibody derivatives produced by enzymatic treatment of a full-length antibody, as well as synthetically produced derivatives, such as recombinantly produced derivatives. Antibody includes an antibody fragment, example of which includes, but not limited to, an Fab, an Fab', an F(ab')$_2$, a single-chain Fv (scFv), an Fv, an dsFv, a diabody, an Fd and an Fd' fragment, and a single domain antibody (dAb) fragment, including a modified fragment (see e.g. Methods in Molecular Biology, Vol 207: Recombinant Antibodies for Cancer Therapy Methods and Protocols (2003); Chapter 1; p 3-25, Kipriyanov; Ward et al., Nature 341: 544-546, 1989, and Wu, A. M. and P. D. Senter. Nat Biotechnol 23(9): 1137-1146(2005)). The fragment may comprise multiple chains linked together, for example by a disulfide linkage and/or by a peptide linker.

As used herein, a full-length antibody is an antibody having two full-length heavy chains (e.g., VH-CH1-CH2-CH3 or VH-CH1-CH2-CH3-CH4) and two full-length light chains (VL-CL) and hinge regions, such as an antibody naturally produced by antibody secreting B cells and a synthetically produced antibody having the same domains.

As used herein, dsFv refers to an Fv having an engineered intermolecular disulfide bond that stabilizes a VH-VL pair.

As used herein, an Fab fragment is an antibody fragment obtained by digestion of a full-length immunoglobulin with papain, or a fragment of the same structure synthesized, for example, by a recombinant method. The Fab fragment comprises a light chain (comprising VL and CL) and another chain comprising a variable domain of heavy chain (VH) and a constant domain of heavy chain (CH1).

As used herein, an F(ab')$_2$ fragment is an antibody fragment resulted from digestion of an immunoglobulin with pepsin at pH 4.0-4.5, or a fragment of the same structure synthesized, for example, by a recombinant method. The F(ab')$_2$ fragment essentially comprises two Fab fragments, wherein each of the heavy chain portions contains several additional amino acids, comprising cysteines that form disulfide bond linking the two fragments.

As used herein, an Fab' fragment is a fragment comprising half of the F(ab')$_2$ fragment (one heavy chain and one light chain).

As used herein, an "Fv" is a minimal antibody fragment that contains a complete antigen recognition and binding site. This fragment consists of a tightly non-covalently associated dimer of a heavy chain variable region domain and a light chain variable region domain. Folding of these two domains produces six hypervariable loops (three loops from each of the H and L chains), contributing amino acid residues for antigen binding and conferring antigen binding specificity to the antibody. A single variable domain (or half of Fv comprising only three CDRs specific for an antigen) also has the ability to recognize and bind the antigen.

As used herein, an scFv fragment refers to an antibody fragment comprising a variable light chain (VL) and a variable heavy chain (VH) covalently linked by a polypeptide linker in any order. The length of the linker is such that the two variable domains can be bridged without interfering each other substantially. An example of the linker is (Gly-Ser)n residues with some Glu or Lys residues to increase solubility. The review about sFv can refer to "The Pharmacology of Monoclonal Antibodies", vol. 113, Rosenburg and Moore eds., Springer-Verlag, New York, pp. 269-315 (1994).

The term "chimeric antibody" refers to an antibody in which the variable region sequence is derived from one species and the constant region sequence is derived from another, such as an antibody in which the variable region sequence is derived from a mouse antibody and the constant region sequence is derived from a human antibody.

The term "diabody" refers to a small antibody fragment prepared by constructing a sFv fragment with a short linker (about 5-10 residues) between VH and VL domains, thereby leading to an interchain rather than intrachain pairing of the V domains, resulting in a bivalent fragment, i.e., a fragment having two antigen binding sites.

Bispecific antibody is a heterodimer of two "cross" sFv fragments in which the VH and VL domains of the two antibodies are present on different polypeptide chains. See, e.g., EP 404,097, WO 93/11161 and Hollinger et al., Proc. Natl. Acad. Sci. USA, 90: 6444-6448 (1993).

"A human antibody" refers to an antibody comprising only human immunoglobulin sequences. If the human antibody is produced in a mouse, in a mouse cell, or in a hybridoma derived from a mouse cell, the human antibody may contain a murine carbohydrate chain. Similarly, "a mouse antibody" or "a rat antibody" refers to an antibody comprising only mouse or rat immunoglobulin sequences, respectively.

A "humanized" antibody refers to a form of a non-human (e.g., mouse) antibody that is a chimeric immunoglobulin, immunoglobulin chain, or fragment thereof (e.g., Fv, Fab, Fab', F(ab')$_2$, or other antigen-binding subsequences of an antibody) containing minimal sequences derived from a non-human immunoglobulin. Preferably, the humanized antibody is a human immunoglobulin (recipient antibody) in which the residues of the complementarity determining regions (CDRs) of the recipient antibody are replaced by CDR residues from a non-human species (donor antibody) such as mouse, rat or rabbit having the desired specificity, affinity and capacity.

Furthermore, in humanization, it is also possible to mutate amino acid residues within CDR1, CDR2 and/or CDR3 regions of VH and/or VL, thereby improving one or more binding properties (e.g., affinity) of the antibody. Mutations can be introduced, for example, by PCR-mediated mutation, the effect of which on antibody binding or other functional properties can be assessed using in vitro or in vivo assays described herein. Typically, conservative mutation is introduced. Such mutation may be amino acid substitution, addition or deletion. In addition, mutations within a CDR are typically no more than one or two. Thus, the humanized antibody of the present invention also encompasses an antibody comprising one or two amino acid mutations within a CDR.

Generally, an immunoglobulin has heavy and light chains. Each heavy and light chain comprises a constant region and a variable region (these regions are also referred to as "domains"). In combination, the heavy and light chain variable regions specifically bind to an antigen. The light and heavy chain variable regions comprise a "framework" region interrupted by three hypervariable regions (also referred to as "complementarity determining regions" or "CDRs"). Ranges of the framework region and CDRs have been determined (see Kabat et al., Sequences of Proteins of Immunological Interest, U.S. Department of Health and Human Services, 1991, which is incorporated herein by reference). The sequences of different light or heavy chain framework regions are relatively conserved within one species.

The CDRs are primarily responsible for binding to an epitope of an antigen. The CDRs of each chain are commonly referred to as CDR1, CDR2 and CDR3, numbered sequentially from the N-terminus, and are also typically identified by the chain in which the particular CDR is located. Thus, the VH CDR3 is located in the antibody heavy chain variable domain from which it was found, while the VL CDR1 is the CDR1 from the antibody light chain variable domain from which it was found.

"VH" or "$V_H$" refers to the variable region of an immunoglobulin heavy chain, comprising the variable region of Fv, scFv, dsFv or Fab. "VL" or "$V_L$" refers to the variable region of an immunoglobulin light chain, comprising the variable region of Fv, scFv, dsFv or Fab.

As used herein, the "monoclonal antibody" or "mAb" or "Mab" refers to a population of substantially homogeneous antibodies, i.e., except for possible natural occurring mutations that may be present in a minor amount, the amino acid sequences of the antibody molecules that make up the population are identical. In contrast, a conventional (polyclonal) antibody preparation typically includes many different antibodies having different amino acid sequences in variable domains, particularly CDRs, which are typically specific for different epitopes. The modifier "monoclonal" means that an antibody is characterized as being obtained from a population of substantially homogeneous antibodies, and should not be construed as requiring any particular method to produce the antibody. For example, a monoclonal antibody to be used in accordance with the present invention can be prepared by the hybridoma method described by Kohler et al. (1975) Nature 256: 495 at first, or by a recombinant DNA method (see, e.g., U.S. Pat. No. 4,816,567). "Monoclonal antibody" can also be isolated from a phage antibody library, for example, using the techniques described in Clackson et al. (1991) Nature 352: 624-628 and Marks et al. (1991) J. Mol. Biol. 222: 581-597. See also Presta (2005) J. Allergy Clin. Immunol. 116: 731.

In another particular embodiment, an antibody or antibody fragment according to the invention comprises a heavy chain variable region (VH) comprising an amino acid sequence as set forth in SEQ ID NO: 1.

In another particular embodiment, an antibody or antibody fragment according to the invention comprises a light chain variable region (VL) comprising an amino acid sequence as set forth in SEQ ID NO: 3 or SEQ ID NO: 145 or an amino acid sequence having at least 95%, 96%, 97%, 98% or 99% identity thereto.

The term "% identity" is determined by comparing two optimally aligned sequences over a comparison window, wherein a portion of a polypeptide sequence in the comparison window may contain an addition or deletion (i.e., gap) as compared to a reference sequence (which does not contain the addition or deletion) to optimally align the two sequences. "% identity" is calculated as follows: the number of positions at which the same nucleic acid bases or amino acid residues occur in both sequences is divided by the total number of positions in the comparison window and the result is multiplied by 100.

In another particular embodiment, an antibody or antibody fragment according to the invention comprises a heavy chain variable region (VH) comprising the amino acid sequence of SEQ ID NO: 1 and a light chain variable region (VL) comprising the amino acid sequence of SEQ ID NO: 3 or SEQ ID NO: 145 or an amino acid sequence having at least 95%, 96%, 97%, 98% or 99% identical thereto.

In another particular embodiment, an antibody according to the invention comprises an amino acid sequence as set forth in SEQ ID NO: 13, SEQ ID NO: 14, SEQ ID NO: 146, amino acids 1-241 of SEQ ID NO: 13, or amino acid residues 1-242 of SEQ ID NO: 13.

In another particular embodiment, an antibody according to the invention comprises an amino acid sequence as set forth in SEQ ID NO: 13. In another particular embodiment, an antibody or antibody fragment according to the invention is a monoclonal antibody having an equilibrium binding dissociation constant (KD) of $1 \times 10^{-8}$ M or less, $1 \times 10^{-9}$ M or less, or $1 \times 10^{-10}$ M or less.

In another particular embodiment, an antibody or antibody fragment according to the invention is a monomer or polymer.

In another particular embodiment, an antibody or antibody fragment according to the invention is an antibody sequence derived from a mammalian antibody sequence, in particular from a human.

In another particular embodiment, the antibody or antibody fragment binds directly to ED-B domain. In particular, the ED-B domain may be an independent ED-B recombinant protein, or a recombinant protein formed by fusing an ED-B protein with other protein(s), or natural fibronectin containing ED-B domain. More particularly, the ED-B domain may be from human, mouse, rat, chicken or other species. More particularly, the ED-B domain may be a glycosylated or a non-glycosylated protein.

In a particular embodiment, the antibody fragment may be a monovalent small molecule antibody such as a single-chain antibody, a single domain antibody, a hypervariable region polypeptide or the like, an Fab, or a multivalent small molecule antibody such as a double-, triple-chain antibody or a mini-antibody.

In another particular embodiment, the antibody is a human immunoglobulin IgG.

In another aspect, the invention provides a pharmaceutical composition comprising an antibody or antibody fragment according to the invention.

In one embodiment, the pharmaceutical composition further comprises, but is not limited to, a fusion protein, a radioisotope, a fluorescent dye, a chemical, a nanoparticle, and the like. In a particular embodiment, the pharmaceutical composition is used for the diagnosis or treatment of a tumor or cancer-related disease.

In yet another aspect, the invention provides the use of an antibody or antibody fragment or pharmaceutical composition according to the invention for the prevention, diagnosis and treatment of a cancer-related disease.

In yet another aspect, the invention provides a method of preventing, diagnosing and treating a cancer-related disease in a subject, comprising administering to the subject a therapeutically or prophylactically effective amount of an antibody or antigen-binding fragment thereof or a pharmaceutical composition according to the invention.

In yet another aspect, the invention provides the use of an antibody or antibody fragment or pharmaceutical composition according to the invention in the manufacture of a medicament for the prevention, diagnosis and treatment of a cancer-related disease.

Particularly, a cancer-related disease according to the invention is a cancer expressing FN(B+) containing ED-B domain. More particularly, the cancer-related disease is gastric cancer, colorectal cancer, lung cancer or breast cancer.

As used herein, "treating" a subject having a disease or disease condition means that the subject's symptom(s) are partially or completely alleviated, or remain unchanged after treatment.

Thus, treatment includes prevention, therapy and/or cure. Prevention refers to prevent a potential disease and/or worsening of a symptom or disease progression. Treatment also includes any medical use of any antibody or antigen-binding fragment thereof provided, as well as the composition provided herein.

As used herein, "therapeutically effective amount" or "therapeutically effective dose" refers to an amount of a substance, compound, material, or composition comprising a compound at least sufficient to produce a therapeutic effect after administration to a subject. Thus, it is the amount necessary to prevent, cure, ameliorate, arrest or partially arrest a symptom of a disease or disorder.

As used herein, "therapeutic effect" means an effect resulted from treatment of an individual that alters, generally ameliorates or improves the symptom(s) of, or cures a disease or disease condition.

As used herein, a "prophylactically effective amount" or "prophylactically effective dose" refers to an amount of a substance, compound, material, or composition comprising a compound that, when administered to a subject, has a desired prophylactic effect, e.g., preventing or delaying the onset or recurrence of a disease or disease condition, and reducing the likelihood of the onset or recurrence of a disease or disease condition. A fully prophylactically effective dose does not have to occur by administration of one dose, and may occur only after administration of a series of doses. Thus, a prophylactically effective amount can be administered in one or more administrations.

As used herein, the term "subject" refers to human and non-human mammals, such as mice, rats, sheep, cattle, dogs, cats, rabbits, and the like.

An antibody or antigen-binding fragment thereof according to the invention or a pharmaceutical composition according to the invention may be administered in one or more ways using one or more methods well-known in the art. It will be appreciated by those skilled in the art that the way and/or manner of administration will vary depending on the desired result. The way of administration according to the invention includes, for example, parenteral administration, such as injection or infusion. As used herein, the phrase "parenteral administration" refers to a way of administration other than enteral and topical administration, typically injection and infusion, including but not limited to intravenous, intramuscular, intra-arterial, intradermal, intraperitoneal and subcutaneous. Alternatively, an antibody or antigen-binding fragment thereof according to the invention for tumors or the pharmaceutical composition according to the invention may also be administered non-parenterally, such as topically, epidermally or mucosally, e.g., intranasally, orally, vaginally, rectally, sublingually or topically.

In yet another aspect, the invention provides a diagnostic kit comprising an antibody or antibody fragment according to the invention, which can be used for in vivo diagnosing distribution of tumor tissues, pathological tissue sections, etc., or for assaying and characterizing cells, proteins, etc., or for affinity purifying cells or protein molecules containing an ED-B domain. The invention further provides the use of a kit according to the invention for in vivo diagnosing distribution of tumor tissues, pathological tissue sections, for assaying and characterizing cells, proteins, or for affinity purifying cells or protein molecules containing an ED-B domain. The invention still further provides the use of a kit according to the invention for preparing a kit used for in vivo diagnosing distribution of tumor tissues, pathological tissue sections, for assaying and characterizing cells, proteins, or for affinity purifying cells or protein molecules containing an ED-B domain.

An antibody or antigen-binding fragment thereof according to the invention contained in the pharmaceutical composition or kit may also be conjugated to a therapeutic moiety such as a cytotoxin, radioisotope or biologically active protein. See, e.g., "Remington's Pharmaceutical Sciences", 19$^{th}$ Edition (Mack Publishing Co. 1995); and Goodman and Gilman, "The Pharmacological Basis of Therapeutics", 7$^{th}$ Edition (MacMillan Publishing Co. 1985).

In another aspect, the invention provides a polynucleotide molecule encoding an antibody or antibody fragment according to the invention.

In a particular embodiment, the polynucleotide molecule comprises a nucleotide sequence encoding an amino acid sequence of the heavy chain variable region of an antibody as set forth in SEQ ID NO: 2 and a nucleotide sequence encoding an amino acid sequence of the light chain variable region of an antibody as set forth in SEQ ID NO: 4.

Conventional symbols are used herein to describe nucleotide sequences: the left end of a single-stranded nucleotide sequence is the 5' end; the left direction of a double-stranded nucleotide sequence is referred to as the 5'-direction. The direction of 5' to 3' addition of nucleotides to a nascent RNA transcript is referred to as the direction of transcription. A DNA strand having the same sequence as mRNA is referred to as "coding strand", a sequence on a DNA strand that has the same sequence as the mRNA transcribed from the DNA and is located 5' to the 5' end of the RNA transcript is referred to as "upstream sequence", and a sequence on a DNA strand that has the same sequence as the RNA and is located 3' to the 3' end of the coding RNA transcript is referred to as "downstream sequence".

In particular, the invention provides a monoclonal antibody (abbreviated as DE2) against the human ED-B protein domain, which is a fully human antibody, comprising a human heavy chain variable region and a light chain variable region, and a linker fragment linking the heavy chain variable region and the light chain variable region. In particular, the DE2 antibody described herein may be a DE2 single-chain antibody (scFv) comprising a heavy chain variable region, a light chain variable region and a linker which are preferably constructed in the form of antibody heavy chain variable region-linker-antibody light chain variable region, wherein the heavy chain variable region comprises an amino acid sequence as set forth in SEQ NO: 1; and the light chain variable region comprises an amino acid sequence as set forth in SEQ ID NO: 3. Preferably, the linker fragment comprises an amino acid sequence as set forth in $(G_4S)_3S$ (SEQ ID NO: 11) or $(G_4S)_3$ (SEQ ID NO: 94). In a particular embodiment, the DE2 antibody comprises an amino acid sequence as set forth in SEQ ID NO: 13.

In yet another aspect, the invention also provides a DNA molecule encoding the monoclonal antibody described above.

In one embodiment, the DNA molecule comprises a nucleotide sequence as set forth in SEQ ID NO: 2 encoding a heavy chain variable region of a monoclonal antibody and a nucleotide sequence as set forth in SEQ ID NO: 4 encoding a light chain variable region of a monoclonal antibody, and optionally a nucleotide sequence as set forth in SEQ ID NO:

12 encoding a linker fragment useful for linking the heavy and light chain variable regions of a monoclonal antibody.

The amino acid sequence of ED-B domain according to the invention can refer to SEQ ID NO: 16.

As used herein, a "monoclonal antibody", also referred to simply as a "monoclonal antibody", refers to a class of highly homogeneous, specific antibodies in which the amino acid sequence and structure of each antibody is identical, except for a few naturally occurring mutations that may occur naturally. A monoclonal antibody recognizes only one antigenic epitope (epitope) and is highly specific. "Monoclonal" refers only to the homogeneity of the source or composition of an antibody and is a description of the characteristics of an antibody, and is not a specific method or technique of production. A monoclonal antibody can be prepared by a number of well-known methods (Smith et al. (2004) J. Clin. Pathol. 57, 912-917; and Nelson et al., J Clin Pathol (2000), 53, 111-117). For example, a monoclonal antibody can be prepared by immortalizing B cells, for example, by fusing with myeloma cells to produce a hybridoma cell line or by infecting B cells with a virus such as EBV. Recombinant techniques may also be used to prepare an antibody in vitro from a cloned population of host cells by transforming the host cells with a plasmid carrying an artificial sequence of nucleotides encoding the antibody.

As used herein, the terms "antibody", "single-chain antibody", "antibody fragment", or "immunoglobulin" each comprise an antibody heavy chain variable region (VH) and light chain variable region (VL), or portions thereof. The heavy and light chains may be linked by a covalent disulfide bond or by an artificially synthesized polypeptide to form a monomer or polymer. Each variable region may be linked to a constant region or fused to other protein(s).

As used herein, the term "variable region" means that certain specified sequences in an antibody differ greatly among different antibodies, and the difference in variable regions results in a specific recognition of a particular antigen or antigenic epitope by antibody. The variable region is at the N-terminus of the heavy and light chains, is a region with greater variation in amino acid sequence and typically has a molecular weight of about 25,000 Daltons. The variable region contains three complementarity determining regions (CDRs, or hypervariable regions), and the more conserved portions between different CDR regions are referred to as framework regions (FRs). CDR regions are regions of an antibody for recognizing and binding to an antigen, and directly determine the specificity of the antibody.

The antibody constant region described herein comprises a heavy chain constant region and a light chain constant region, and the heavy chain constant region can be divided into five types according to the difference classification of amino acid sequences, including IgA, IgD, IgE, IgG and IgM, some of which may be further subdivided into subclasses; the light chain constant region can be divided into κ and λ, respectively.

A "fusion protein" as used herein refers to a protein formed by two or more natural proteins or artificially modified proteins which are linked in series by genetic engineering techniques, and the original proteins may be linked by an artificially designed polypeptide fragment or directly by a peptide bond. Reference herein is generally to a fusion form of an antibody with other protein(s), such as with other antibody to form a bispecific antibody or multispecific antibody; with a cytokine such as interleukin-2 (IL-2), interleukin-15 (IL-15), interleukin-12 (IL-12), tumor necrosis factor α (TNF α) to form a fusion protein; with a protein toxoid and a partial polypeptide sequence or a subunit of a toxin, including plant toxins (e.g., ricin), bacterial toxins (e.g., cholera toxin), animal toxins (e.g., melittin), and fungal toxins. The techniques used are well-known to those skilled in the art.

As used herein, a novel drug molecule formed by antibody-drug conjugates (ADCs) refers to a novel compound formed by an antibody and a chemical, including an antimitotic agent, an alkylating agent, an antimetabolite, an anticancer agent, an antiangiogenic agent, an apoptotic agent, an alkaloid, an antibiotic, or a combination thereof, through a covalent reaction.

As used herein, "polymer" refers to a polymer formed by a plurality of protein monomers in a covalent or non-covalent form. For example, human antibody IgGs are typically covalently bound by disulfide bonds to form a tetramer.

As used herein, the term "radioisotope" refers to a radioactive nuclide, typically iodine 131, iodine 125, lutetium 177, etc. An immunotherapeutic agent with radioactivity prepared by labeling an antibody with high specificity and affinity for an antigen with a radioisotope can reach a target organ after being injected into body and exert the biological effect of radiation, and can also be used in the diagnosis.

A "pharmaceutical composition" as used herein refers to a new drug formed by cross-linking an antibody or an antibody fragment with other chemical(s) or radioisotope(s) through a chemical bond; also to a fusion protein of an antibody or an antibody fragment with other protein(s) such as a cytotoxin and expressed by a cell; also to a novel targeting agent generated by linking an antibody or an antibody fragment to the surface of a nanoparticle; also included are a composition comprising the antibody, the antibody fragment, the novel drug, the fusion protein or the agent as described above and a pharmaceutically acceptable carrier.

A major component of the "kit" described herein is the antibody or antibody fusion protein described herein, or a novel antibody composition with a labeling fluorescein, radioisotope, peroxidase, alkaline phosphatase and the like based thereon, optionally containing a buffer, an antibody not described herein, a substrate for an enzymatic reaction such as diaminobenzidine (DAB), and the like, and a corresponding support such as an ELISA plate, magnetic beads, and the like. The kit can be used in the diagnosis of in vivo distribution of tumor tissues, pathological tissue sections and the like, or for assaying and characterizing a cell, a protein and the like, or for affinity purifying cells or a protein molecule containing an ED-B protein domain.

The "diagnosis" method described herein refers to a qualitative or quantitative detection of a substance that reflects the health status of a human body, such as human body fluid, blood, and tissue, and the commonly used experimental techniques include immunohistochemistry, immunocytochemistry, enzyme-ligated immunosorbent assay, etc.

The "treatment" method described herein refers to a process of applying an antibody or an antibody fragment or a drug combination formed by the antibody or the antibody fragment via intravenous injection or local focus injection which could reach a tumor tissue after entering body and exert the drug effect.

The invention provides an antibody capable of specifically recognizing an ED-B protein, comprising a heavy chain variable region amino acid sequence as set forth in SEQ NO: 1 and a light chain variable region amino acid sequence as set forth in SEQ NO: 3 or SEQ ID NO: 145. The antibody may also exert its biological functions in a variety of forms, but basically, the antibody fragment comprises the CDR3 region sequence of the heavy chain or the CDR3 region sequence of the light chain.

The invention also provides a DNA sequence encoding the antibody. In one example, the DNA comprises a nucleotide sequence as set forth in SEQ ID NO: 2, which encodes an antibody heavy chain variable region amino acid sequence, and/or the DNA comprises a nucleotide sequence as set forth in SEQ ID NO: 4 or 147, which encodes an antibody light chain variable region amino acid sequence.

The invention further provides a method of preparing the monoclonal antibody above.

Once the amino acid or nucleotide sequence encoding an antibody according to the invention is obtained, a fully human monoclonal antibody according to the invention can be prepared by those skilled in the art using conventional methods in the art, for example, by hybridoma technology or genetic engineering technology well-known to those skilled in the art, or can be obtained by screening hybridoma cell strains or by separating via phage antibody library display technology.

As used herein, the term "hybridoma" or "hybridoma cell" refers to a cell or cell line (typically a myeloma or lymphoma cell) produced by fusing an antibody-producing lymphocyte with a cancer cell not producing antibody. As known to those of ordinary skill in the art, hybridomas can proliferate and continue to produce a specific monoclonal antibody. Methods for producing hybridomas are known in the art (see e.g. Harlow & Lane, 1988). Reference to the term "hybridoma" or "hybridoma cell" also includes subclones and progeny cells of the hybridoma.

An ED-B monoclonal antibody according to the invention can be obtained by cloning the single-chain antibody nucleotide sequence provided by the invention into a protein expression vector, or respectively cloning the antibody heavy chain nucleotide sequence and the antibody light chain nucleotide sequence into different expression vectors or the same vector.

The protein expression vectors described herein include, but not limited to, prokaryotic cell protein expression vectors, yeast cell protein expression vectors, insect cell protein expression vectors, plant cell protein expression vectors, and mammalian cell protein expression vectors, which contain the functional elements required for expression of a protein in corresponding host cells, such as a promoter, a terminator, a resistance screening fragment, and the like.

A DNA sequence encoding a monoclonal antibody according to the invention can be obtained by a means well-known to those skilled in the art, such as by DNA sequence inference based on the amino acid sequence, or by reverse transcription by extracting mRNA, or directly by artificially synthetic methods. These DNA sequences are then inserted into expression vectors by a means such as enzymatic restriction and ligation, and the DNA sequence encoding the antibody is in an appropriate reading frame with a necessary start codon and a stop codon. The expression vectors used in the invention are various commercial expression vectors well-known to those skilled in the art.

The constructed expression vector is transformed or transfected into an appropriate host cell, and the antibody protein can be expressed under suitable culture conditions.

"Host cell" includes a prokaryotic cell, a eukaryotic cell, and the like. In the present application, a eukaryotic host cell is preferable, and a mammalian cell is more preferable, which is commercially available or available in cooperative units, including but not limited to, Chinese hamster ovary cells (CHO), human embryonic kidney cells (HEK293), African green monkey kidney cells (Vero), baby hamster kidney cells (BHK), African green monkey kidney cells (COS), and other various immortalized cell lines. CHO and HEK293 cells are generally used as host cells in the invention, and it is well-accepted in the art that these cell strains are capable of providing correct translation, protein folding, disulfide bond formation, glycosylation and other modifications to a protein molecule to the natural state of a human protein. However, it is well-known to those skilled in the art that the various cell lines mentioned above and their derivatives can express an antibody or fusion protein according to the invention.

A method for transforming or transfecting a host cell with an expression vector includes electroporation, a liposome-mediated method, calcium phosphate precipitation, a PEI-mediated method and the like, and those skilled in the art can employ an appropriate transfection method according to different host cells and purposes. For example, HEK293 cells are transfected with a PEI-mediated vector containing an antibody nucleotide sequence, while CHO cells are transfected with a liposome from Invitrogen for the construction of a cell strain stably expressing an antibody.

The purification of an antibody according to the invention is determined according to the characteristics of the protein or the used protein tag, for example, an antibody containing a constant region fragment of an antibody can be subjected to Protein A affinity chromatography; or an antibody containing a 6× histidine tag can be subjected to nickel column affinity chromatography, or ion exchange chromatography, hydrophobic chromatography, molecular sieve chromatography, dialysis, gel electrophoresis and the like. An antibody according to the invention or a fusion protein containing the antibody can be obtained by those skilled in the art using a conventional isolation and purification method.

An antibody according to the invention can be characterized using a variety of methods, such as enzyme-ligated immunosorbent assay (ELISA), Western Blot, and affinity assay can be carried out using BIAcore technology or Scatchard assay (Beatty et al. J Immunol Methods 1987, 173-179).

An antibody or antibody fragment according to the invention can be labeled with a chemical such as a fluorescent dye or a radioisotope for in vivo or in vitro tracing. In one specific embodiment, after an antibody is labeled with Cy5.5 fluorescent dye, its distribution or metabolism in a mouse body can be analyzed through a fluorescence imager, and a solid tumor with high expression of an ED-B in a mouse body can also be detected through the method.

An antibody or antibody fragment according to the invention can be labeled with a fluorescent dye or a biologically active enzyme for in vitro detection or experimental studies. In one specific embodiment, an antibody is labeled with a FITC fluorescent dye and used to detect the expression of ED-B in tissues or cells. In particular, an antibody according to the invention can also be without any label, and the above-mentioned detection can be realized by means of a secondary antibody with a fluorescent dye or a bioactive enzyme label, and the related antibody application methods and experimental techniques can be realized by those skilled in the art through conventional technical means.

An antibody or antibody fragment according to the invention can be fused with various proteins or coupled with chemical drugs, radioisotopes, nanoparticles and the like, to play a targeting effect to form a targeting drug. The efficacy of an antibody or antibody fragment and the corresponding targeting drug according to the invention can be verified at the cellular level or the living body level, which can be realized by those skilled in the art via conventional drug experimental methods.

Unless defined otherwise, all technical and scientific terms used herein have the same meanings as commonly understood by those skilled in the art, to which this disclosure belongs. All references cited herein, including patents, patent applications, articles, textbooks, publications, GenBank sequences, websites, and other published materials, and the like, and the references cited therein, are hereby incorporated by reference in their entireties. In case of conflict, the present specification, including definitions, will control. It will be apparent to those skilled in the art that various changes and modifications can be made to the above-described description or embodiments of the invention without departing from the spirit and scope of the invention, and it is intended that the appended claims cover all such modifications that are within the scope of the invention.

In addition, a singular term shall include the plural and a plural term shall include the singular, unless specifically required. Similarly, the word "or" is intended to include "and" unless it is clearly indicated by the context otherwise. The techniques and methods described herein are generally carried out according to conventional methods well-known in the art and described in the references cited in this specification. It should also be understood that all base sizes or amino acid sizes as well as all molecular weights or molecular mass values for a given nucleic acid or polypeptide are approximate and are for illustration only.

The invention will now be further described with reference to examples. It should be understood, however, that the examples are for illustration and not intended to limit the invention.

EXAMPLES

The invention is further illustrated by the following examples, but any example or combination thereof should not be construed as limiting the scope or embodiments of the invention. The scope of the invention is defined by the appended claims; and along with the description and general knowledge in the art, the scope of the claims will be clear to those skilled in the art. Those skilled in the art can make any modifications or variations to the technical solutions of the invention without departing from the spirit and scope of the invention, and such modifications and variations also fall within the scope of the present invention.

Example 1: Panning of Human Single-Chain Antibody Specific for ED-B Domain in Human FN 1) ED-B gene (SEQ ID NO: 16) was cloned into pET-22b(+) (Novagen) by EcoRI and NotI endonuclease restriction sites using conventional molecular cloning methods and expressed in *Escherichia coli*. A six-histidine tag was introduced at the C-terminus of the ED-B and used to obtain a purified protein by affinity chromatography. Other type Ill domains in FN, FN-789 (containing FN-7, FN-8 and FN-9) and FN-7B89 (containing FN-7, ED-B, FN-8 and FN-9), were expressed and purified in the same manner, and the respective sequences were obtained with reference to the literature (Leahy, Aukhil et al. Cell 1996, 155-164, and Schiefner, Gebauer et al. J Biol Chem 2012, 17578-17588).

2) Construction of an Antibody Library

A library of fully human synthetic antibodies was designed for panning a single-chain antibody against the antigen ED-B. DP47, the most common heavy chain template in human antibody molecules (Tomlinson, I. M., Walter, G., Marks, J. D., Llewelyn, M. B. & Winter, G. (1992), The repertoire of human germline VH segments reveals about fifty groups of VH segments with different hypervariable loops. J. Mol. Biol., 227, 776-798) was used as the heavy chain template, and DPL11 (Williams, S. C. & Winter, G. (1993), Cloning and sequencing of human immunoglobulin V lambda gene segments. Eur. J. Immunol., 23, 1456-1461) was used as the light chain template, which were linked together using the DNA corresponding to the commonly used peptide $(G_4S)_3S$ (SEQ ID NO: 11) to form a single-chain antibody library template in which the CDR regions of the light and heavy chains were randomly added empirically. Specifically, besides the heavy chain CDR3 region and the light chain CDR3 region of the DNA template of this antibody library were randomly added, other sequences refer to the A11 nucleotide sequence as set forth in SEQ ID NO: 15. The template was obtained by chemical synthesis. Primer sequences for construction of the random antibody library are shown in the following table. Using the above synthetic library as template, fragments DP47 and DPL11 containing random sequences were cloned with a pair of primers DP47EcoRback and DP47for and another pair of primers DP47FR4back and DPL11for, respectively, and then using purified DP47 and DPL11 as mixed template, PCR amplification was carried out with primers DP47EcoRback and DPL11NotIfor to obtain a single-chain antibody DNA fragment containing random sequences. The heavy chain and the light chain in the single-chain antibody DNA fragment respectively consist of DP47 and DPL11, and the random sequences in the heavy chain and the light chain are respectively introduced by DP47for and DPL11 for primers. The EcoRI and NotI restriction sites were introduced into the 5' and 3' ends of the single-chain antibody DNA fragments by the primers DP47EcoBack and DPL11NotIfor, respectively, and by these restriction sites, the DNA fragment was constructed into the multiple cloning sites of pCANTAB5E (Amersham Biosciences) plasmid vector for construction of plasmids producing a random antibody library. Plasmids were transformed into *Escherichia coli* TG1 by electroporation for the next phage antibody library display and antibody panning.

| Primer Name | Primer Sequence |
|---|---|
| DP47EcoRback | GGCGAATTCCGAAGTGCAGCTGTTG (SEQ ID NO: 17) |
| DP47for | TGCCCTGGCCCCAGTAATCGAAMNNMNNMNNMNNA CGCGCACAGTAATATACGGCG (SEQ ID NO: 18) |
| DP47FR4back | TTCGATTACTGGGGCCAGGGCACCCTGGTC (SEQ ID NO: 19) |
| DPL11for | TTTAGTGCCACCGCCGAAGACMNNMNNMNNMNNATCCC ATGACTGGCAGTAATAATCAGC (SEQ ID NO: 20) |
| DPL11NotIfor | ATAAGAATGCGGCCGCACCCAGCACAGTCAGTTTAGT GCCACCGCCGAAGAC (SEQ ID NO: 21) |

Note:
N is any nucleotide selected from A, C, G or T, and M is any nucleotide selected from A or C.

3) Phage Antibody Library Display and Antibody Panning

Referring to recombinant phage panning user manual of Amersham Biosciences (Expression module/Recombinant Phage Antibody system product insert, Pharmacia Biotech document XY-040-00-08). Briefly, 50 µl of antibody library *Escherichia coli* TG1 broth was added to 50 ml of fresh 2×YT medium and cultured with shaking at 37° C. until OD value was 0.4-0.5. Helper phage was added to infect at 37° C. for 30 min, and after precipitated with PEG8000 (Bio-engineering Co., Ltd.), centrifuged at 10000 g for 30 min and re-suspended in PBS for later use. The titer of the prepared antibody fusion phage library should be above $10^{12}$ CFU/ml.

The EDB antigen (SEQ ID NO: 16) was coated on a 5 ml immune tube, blocked with milk and incubated with 2 ml of the above prepared PBS solution of the phage antibody library at 37° C. for 2 hours, decanting the liquid in the immune tube, washed 20 times with PBS containing 0.1% Tween-20, adding 4 ml of TG1 bacteria in log phase and incubating standstill at 37° C. for 1 hour. The bacterial liquid was coated on an SOB plate containing ampicillin and glucose, cultured overnight to collect *Escherichia coli* TG1 bacterial liquid infected with phage, and the first round of panning was completed. The obtained TG1 bacterial liquid was used to prepare an antibody fusion phage library to go through a second round of panning.

Three rounds of panning were carried out with the ED-B as antigen, and the obtained *Escherichia coli* TG1 was diluted in proper proportion and then coated on an agarose plate to obtain single colonies, which were respectively used to express soluble antibodies for ELISA detection, and phage clones with the highest color development under the conditions of the same coated antigen were selected for further analysis.

4) Cloning of an Antibody from a Prokaryotic Vector to an Eukaryotic Vector

The DNA fragment of the single-chain antibody obtained by panning was digested with enzymes EcoR I and Not I and then ligated into a pCl-neo (Promega) vector containing a DNA sequence encoding the constant region Fc fragment of human IgG1 antibody, and the DNA sequence of the antibody and the DNA sequence of the IgG1 Fc were in the same open reading frame, so that a fusion protein of them can be expressed, wherein the IgG1Fc is at the C end of the fusion protein, and can be used for purifying of the single-chain antibody and improving the stability of the antibody protein. The antibody DE2-Fc (SEQ ID NO: 13) or L19-Fc used in the following Examples 3, 4, 5 and 8 are single-chain antibody recombinant proteins with IgG1Fc.

5) Eukaryotic Expression of Antibody Protein

Inoculation was with an initial density of 500,000 cells/ml in the day prior to transfection, and the cells were centrifuged (100 g, 5 min) when the cells reached to 1,000,000 cells/ml. The supernatant was discarded and the cells were rinsed with 3 mL of SFM4Transfx293 (Hyclone), and then the supernatant was discarded and the cells were re-suspended in an equal volume of SFM4Transfx293 medium.

Preparation of transfection complex: 60 µg of DNA was added to 1 mL of pre-warmed PBS (Hyclone, SH30256.01B), mixed gently and left standstill at room temperature to form solution A. 120 µl of PEI (1 mg/ml) was added to 1 mL of pre-warmed PBS and vortexed well to form solution B. The solution B was added into the solution A, pipetted gently and evenly with the tip, and left standstill for 15-25 min at room temperature. The above transfection complex was added to 20 ml of the cell culture system, and cultured. An equal volume of the protein expression medium SFM4HEK293 (Hyclone, SH30521.02) was added directly in the next day and continued to culture. After 4 days of transfection, the medium was collected by centrifugation (800 rpm, 10 min) for protein purification. The purified protein was confirmed by direct ELISA (the antigen coating the solid-phase support was the ED-B protein, the primary antibody was Fc antibody-containing cell culture solution to be detected, and the secondary antibody was HRP-labeled mouse anti-human IgG) and SDS-PAGE experiments that the target protein was obtained, and the yield of the antibody protein was about 40 mg/L.

6) Purification of Monoclonal Antibody

The His-tagged protein was purified by Ni affinity chromatography column (Qiagen) and the antibody with the IgG1 constant region Fc was purified by Protein A affinity column (Genscript), according to the corresponding manufacturer's instructions.

By assaying the antibody protein expressed by mammalian cells and purified directly with ELISA (the solid-phase support was coated with the antigen protein ED-B, the primary antibody was the purified Fc-containing antibody, and the secondary antibody was HRP-labeled mouse anti-human IgG), the A11 antibody according to the invention was obtained. The affinity of the A11 antibody (using Scatchard analysis, c.f. Beatty et al. J Immunol Methods 1987, 173-179) was significantly higher than that of L19, about 3-fold higher than that of L19, comparable to the B5 antibody. The amino acid sequence of the A11 antibody is set forth in SEQ ID NO: 14.

Example 2: Antibody Affinity Maturation

1) Construction of Phage A11 Antibody Sub-Library

To obtain an antibody mutant with higher affinity, the A11 was selected and its encoding DNA sequence was SEQ ID NO: 15. The light chain CDR1: SGDSLGIGSNNYVS (SEQ ID NO: 143) and CDR2: DDNKRPS (SEQ ID NO: 144) regions of the A11 antibody was randomly mutated as follows: the first round of PCR amplification was carried out by using the A11 antibody DNA sequence as a template with the primers DPL11CDR1back and DPL11CDR2for in the following table, and the obtained product was purified and then subjected to the second round of PCR amplification by using the primers DPL11Pstlback and DPL11Aglfor, and the obtained product was cloned into the phagemid vector pCANTAB5E-A11 (i.e. the plasmid vector pCANTAB5E containing the A11 antibody sequence in example 1) by means of the PstI and AgeI restriction sites introduced by the primers to generate a full synthetic ha e single-chain antibody sub-library.

| | |
|---|---|
| DPL11Pstlback | ATCACCATCTCCTGCAGCGGTGATAGCCTGGGTATT (SEQ ID NO: 22) |
| DPL11CDR1back | CAGCGGTGATAGCCTGGGTATTNNKNNKNNKNNKNNN KGTCTCCTGGTACCAACAGCACC (SEQ ID NO: 23) |
| DPL11CDR2for | GGTTAGAAACGCCTGAGGGGCGMNNMNNMNNMNNAT AAATCATGAGTTTGGGGGCT (SEQ ID NO: 24) |
| DPL11Agelfor | TTGGAGCCAGAGAACCGGTTAGAAACGCCTGAGGGG CG (SEQ ID NO: 25) |

Note:
N is any nucleotide selected from A, C, G or T; M is any nucleotide selected from A or C; and K is any nucleotide selected from T or G.

2) Panning of High Affinity Mutants from the Antibody Sub-Library

Four rounds of solid phase panning were performed using the A11 antibody sub-library constructed in this example with the prokaryotically expressed ED-B as antigen. The products of the last three rounds of panning were subjected to single colony phage display and positive clones were preliminarily identified by ELISA using prokaryotically expressed soluble antibody proteins. Further activity characterization was performed by eukaryotically expressed antibody proteins by HEK293T (from Boster Biological Technology Co., Ltd.). The specific methods for panning, antibody expression, and positive clone identification were the same as the Example 1.

3) Panning Results

Among the most chromogenic phage positive clones obtained by panning, 50 were selected for sequencing. 47 sequencing maps were obtained, and 24 different sequences were obtained. Among them, 32 sequences had repeats, in which the most frequently repeated were CB33, DE2 and CA5, the next were CA12 and CD1, and the 15 sequences were single sequences. Increasing the number of sequencing samples could increase the number of enriched repeat sequences.

| Sequence Name | LCDR1 Mutant Residue | SEQ ID NO: | LCDR2 Mutant Residue | SEQ ID NO: | Number of Enrichment |
|---|---|---|---|---|---|
| CB3 | AWSSA | 26 | SASE | 50 | 5 |
| DE2 | FRSGM | 27 | LPTS | 51 | 5 |
| CA5 | RAFTP | 28 | QSHW | 52 | 5 |
| CA12 | RLPPG | 29 | SNTT | 53 | 4 |
| CD1 | SRSTY | 30 | SAEL | 54 | 4 |
| CB2 | PGFSP | 31 | SYRS | 55 | 3 |
| CA1 | HMPPY | 32 | SSQH | 56 | 2 |
| CD7 | LARSP | 33 | SHGR | 57 | 2 |
| DE1 | LWLSP | 34 | WSND | 58 | 2 |
| DF3 | AWSSS | 35 | FRVS | 59 | 1 |
| CB4 | CPLVS | 36 | SAYL | 60 | 1 |
| DF1 | FLPGR | 37 | DLMS | 61 | 1 |
| DH3 | GWSGS | 38 | LKSQ | 62 | 1 |
| DE10 | LGSGP | 39 | LPTF | 63 | 1 |
| CA2 | LRPAP | 40 | ANEL | 64 | 1 |
| CD4 | PARSP | 41 | PRTP | 65 | 1 |
| DG2 | PSFSP | 42 | PNAR | 66 | 1 |
| CA3 | PWVSG | 43 | PSDH | 67 | 1 |
| CB7 | RLFLP | 44 | ASQS | 68 | 1 |
| CC3 | SRSRY | 45 | SAEL | 69 | 1 |
| CB1 | SRSTY | 46 | SAKL | 70 | 1 |
| CC2 | TQSKY | 47 | SAEL | 71 | 1 |
| DE4 | VRSLG | 48 | LNGR | 72 | 1 |
| DE6 | WLCGP | 49 | LPRS | 73 | 1 |

The antibody obtained by HEK293T expression was used for ELISA affinity assay (see Beatty et al. J Immunol Methods 1987, 173-179), and the antibody with higher affinity was preferably used as a candidate antibody. The relative affinities of mutant antibodies were assayed by ELISA, and all the obtained new antibodies could specifically bind to the ED-B with an affinity equal to or significantly higher than that of A11. The affinity of DE2 antibody was the highest and the results of repeated experiments were consistent. The affinities of CB3, CA5, CD1 and CB2 antibodies were basically the same and slightly lower than that of DE2. DE2 antibody was included in candidate antibodies for further analysis.

Based on primer sequences used, the light chain CDR1 and CDR2 sequences of the antibodies described above are shown in the following table.

| Sequence Name | LCDR1 | SEQ ID NO: | LCDR2 | SEQ ID NO: |
|---|---|---|---|---|
| CB3 | SGDSLGIAWSSAVS | 95 | SASERPS | 119 |
| DE2 | SGDSLGIFRSGMVS | 96 | LPTSRPS | 120 |
| CA5 | SGDSLGIRAFTPVS | 97 | QSHWRPS | 121 |
| CA12 | SGDSLGIRLPPGVS | 98 | SNTTRPS | 122 |
| CD1 | SGDSLGISRSTYVS | 99 | SAELRPS | 123 |
| CB2 | SGDSLGIPGFSPVS | 100 | SYRSRPS | 124 |
| CA1 | SGDSLGIHMPPYVS | 101 | SSQHRPS | 125 |
| CD7 | SGDSLGILARSPVS | 102 | SHGRRPS | 126 |
| DE1 | SGDSLGILWLSPVS | 103 | WSNDRPS | 127 |
| DF3 | SGDSLGIAWSSSVS | 104 | FRVSRPS | 128 |
| CB4 | SGDSLGICPLVSVS | 105 | SAYLRPS | 129 |
| DF1 | SGDSLGIFLPGRVS | 106 | DLMSRPS | 130 |
| DH3 | SGDSLGIGWSGSVS | 107 | LKSQRPS | 131 |
| DE10 | SGDSLGILGSGPVS | 108 | LPTFRPS | 132 |
| CA2 | SGDSLGILRPAPVS | 109 | ANELRPS | 133 |
| CD4 | SGDSLGIPARSPVS | 110 | PRTPRPS | 134 |
| DG2 | SGDSLGIPSFSPVS | 111 | PNARRPS | 135 |
| CA3 | SGDSLGIPWVSGVS | 112 | PSDHRPS | 136 |
| CB7 | SGDSLGIRLFLPVS | 113 | ASQSRPS | 137 |
| CC3 | SGDSLGISRSRYVS | 114 | SAELRPS | 138 |
| CB1 | SGDSLGISRSTYVS | 115 | SAKLRPS | 139 |
| CC2 | SGDSLGITQSKYVS | 116 | SAELRPS | 140 |

-continued

| Sequence Name | LCDR1 | SEQ ID NO: | LCDR2 | SEQ ID NO: |
|---|---|---|---|---|
| DE4 | SGDSLGIVRSLGVS | 117 | LNGRRPS | 141 |
| DE6 | SGDSLGIWLCGPVS | 118 | LPRSRPS | 142 |

In addition, it is shown from the above results that if the CDR3 region of the candidate antibodies was unchanged, after modification to non-CDR3 regions (e.g., the light chain CDR1, CDR2 or heavy chain CDR1, CDR2 regions), the affinity of the antibody was changed and the affinity of some mutants was significantly improved. Single point mutation in a CDR region of an antibody generally does not alter the specificity of the antibody, such as the antibody CD1 and the antibody CC3 light chain CDR1 region after affinity maturation of A11 antibody. Similarly, multiple point mutations in a CDR region of an antibody generally do not alter the specificity of the antibody, such as the antibody CB1 and the antibody CC3 light chain CDR1 region after affinity maturation of A11 antibody. However, mutations in a CDR region of a candidate antibody may alter the affinity of the antibody.

Example 3: Antibody Immunofluorescence Labeling

1) FITC Labeling of Antibody

The antibody was dissolved in 0.1 M of carbonate buffer (pH=9.5) to a final concentration of 2 mg/ml. A DMSO solution of FITC was freshly prepared in a final concentration of 1 mg/ml in dark. FITC was slowly added into a protein solution at intervals by a mass ratio of the antibody to the FITC of 10:1, and stirred while adding to uniformly mix the FITC and the antibody; after addition, the solution was mixed for 1 hour and reacted in the dark overnight (in a refrigerator at 4° C.). 5 mol/L of $NH_4Cl$ was added to a final concentration of 50 mM and mixed at 4° C. for 2 hours to stop the reaction. By using HiTrap Desalting pre-load column from the company GE, rapid desalting was carried out with Sephadex G-25 filler and the product was stored as required. The fluorescent dye needs to be protected from light in use.

2) Cy5.5 NHS Ester Labeling of Antibody

The antibody was dissolved in 0.1 M of carbonate buffer (PH=9.0) to a final concentration of 2 mg/ml. A DMSO solution of Cy5.5 NHS Ester (GE Healthcare) was freshly prepared at a final concentration of 1 mg/ml in dark. Cy5.5 NHS Ester was slowly added into the protein solution at intervals by a mass ratio of the antibody to the Cy5.5 NHS Ester of 10:1, and stirred while adding to uniformly mix the Cy5.5 NHS Ester and the antibody; after addition, the solution was reacted in dark for 4 hours at room temperature. By using HiTrap Desalting pre-load column from the company GE, rapid desalting was performed with Sephadex G-25 filler as required, and the product was stored as required. The fluorescent dye needs to be protected from light in use.

Example 4: Specific Detection of Antibody

1) Specific Detection at the Molecular Level

Three proteins, FN-789, FN-7B89 and ED-B (same as example 1), were used as antigens, and after blocked with milk, ELISA assay was carried out by using DE2 antibody as the primary antibody, the rabbit anti-human IgG antibody labeled with horseradish peroxidase as the secondary antibody, and TMB as substrate. The experimental results indicated (FIG. 2) that the DE2 antibody can specifically bind to the ED-B protein and the FN-7B89 protein containing the ED-B domain, but cannot bind to the FN-789 protein without the ED-B.

2) Specific Detection at the Cellular Level

The FN-7B89, containing the transmembrane region W968-K989 of the integrin alpha-IIb (Li, R., et al. (2004). J Biol Chem 279(25): 26666-26673) at the carboxyl end, was constructed into the pCl-neo plasmid which was then transiently transfected CHO-K1 cells (Boster Biological Technology Co., Ltd.) to obtain a CHO-K1 cell strain expressing the FN-7B89 across the membrane and designated as CHO-7B89, the ED-B expression on the cell membrane surface of which was positive. A CHO-K1 cell strain expressing the FN-789 across the membrane was established and designated as CHO-789, the ED-B of which was negative.

10 mL of each of the cells CHO-7B89 and CHO-789 ($200 \times 10^4$/mL) was centrifuged at 600 rpm for 5 min; the supernatant was discarded, washed once with PBS (Hyclone, SH30256.01B) at 37° C. Single cell suspension was obtained by filtering through 100 mesh. The cells were counted and re-suspended in PBS, divided into 8 groups, each having one million cells. The antibodies were labeled as described in example 3.

Sample 1: the antibody was the FITC-labeled L19-Fc, at a concentration of 50 ng/μl and 100 μl in total.

Sample 2: the antibody was the FITC-labeled DE2-Fc, at a concentration of 50 ng/μl and 100 μl in total.

The labeled antibodies were added, incubated at room temperature for 1 hour, and centrifuged at 800 rpm for 5 min. The cells were re-suspended in 1 ml of cold PBS, centrifuged at 800 rpm for 5 min, and unbound antibodies were washed off, and repeating washing once. An anti-fluorescence quenching mounting agent (Boster Biological Technology Co., Ltd.) was added to protect cell morphology. Detection was by a fluorescence microscope.

The results showed (FIG. 3) that the DE2 antibody specifically bound to the CHO-7B89 cells, but the experimental results of the CHO-789 cells were negative, which was the same as that of the L19 antibody.

Example 5: Antibody Affinity Assay

1) Determination of the Absolute Affinity of an Antibody Against the Antigen ED-B by ELISA Scatchard assay was used for affinity assay (Beatty et al. J Immunol Methods 1987, 173-179). 0.1 μg/μl of the antigen ED-B was diluted in four concentration gradients, 1:1, 1:2, 1:4, 1:8 folds and to coat an ELISA plate. After incubated overnight at 4° C., the plate was blocked with 4% skim milk powder. The single-chain antibody diluted by a 3-fold series of gradient was added, the initial concentration of the antibody being 10 μg/ml, and reacted for 1 hour at room temperature, thereafter the horseradish peroxidase-labeled rabbit anti-human IgG antibody was added for 1 hour, and tetramethylbenzidine (TMB) was added for development to an appropriate depth. The reaction was stopped by addition of 2M $H_2SO_4$, and the OD450 absorbance value was measured.

The results from calculation showed that the equilibrium dissociation constant KD of the DE2 antibody was 0.37 nM and the equilibrium dissociation constant KD of the CC3 antibody was 1.18 nM.

The equilibrium dissociation constant KD of the L19 antibody was 6.00 nM, i.e. the affinity of the DE2 and CC3 antibody was higher than that of L19.

2) Determination of the Absolute Affinity of an Antibody Against the Antigen ED-B by Biocore 3000.

Monolayer carboxyl chip CM5 (GE, BR100012) (coupled to the amino group of a protein) was used. For coating, the antigen EDB diluted by acetate buffer (pH=4) (at a concentration of 10 μg/ml) as the stationary phase. The chip was blocked with 1 M ethanolamine-HCl buffer (pH=8.5).

When the kinetic constant was determined, an appropriate antibody concentration gradient was selected, and the antibody concentration was diluted downwards by a 1:2 gradient, and eight concentrations in total were served as mobile phase, each concentration was injected in parallel three times, and the dynamic binding and dissociation of the two proteins were detected by BIAcore 3000.

The equilibrium dissociation constant $K_d$ of DE2 antibody was 93.6 pM; and the equilibrium dissociation constant $K_d$ of the CC3 antibody was 325 pM.

The reported affinity of the L19 antibody determined by BIAcore has a $k_{on}$ of $1.1 \times 10^5$, a $k_{off}$ of $9.6 \times 10^{-5}$, and thus $K_d = 8.7 \times 10^{-10}$ M, i.e. the affinity of the L19 was 872.7 pM (Pini, Viti et al. J Biol Chem 1998, 21769-21776). The affinity of the DE2 antibody detected by this method was also significantly higher than that of the L19.

Example 6: Distribution of the Monoclonal Antibody (1) Biodistribution of the Monoclonal Antibody BALB/c Nude mice (6-8 weeks old, female, SPF grade), in vitro cultured mouse teratoma cells F9 (from Shanghai Fuxiang Biotechnology Co., Ltd.) were injected subcutaneously for modeling, 3 million of F9 cells per implantation site, and solid tumors occurred in the mice 5 days later. Antibody DE2-Cy5.5 (labeled antibody as described in Example 3) was injected via the tail vein at 10 μg/mouse 9 days after modeling and a small animal living-body imager (Xenogen) was used for imaging after 24 hours.

Living-body imaging (FIG. 4) showed that tumor tissues implanted via the FN(B+)-high-expressing F9 cells had very strong near-infrared fluorescence, stronger near-infrared fluorescence was occasionally observed in the bladder, and the fluorescence intensity of other sites was very weak or difficult to detect, indicating that the DE2-Cy5.5 fluorescent dye focused on the tumor tissues.

The experiments also showed that the DE2 antibody has a targeting effect in organisms, can focus on the ED-B expressing tumor tissues, and the carried indicator substance such as Cy5.5 can be used for analyzing information such as tumor site and size, namely, for tumor diagnosis.

(2) Tissue Distribution of the Monoclonal Antibody

After 16 hours of the intravenous injection of 10 μg of the Cy5.5-labeled DE2 antibody (labeled antibody as described in Example 3) into mice, tumor tissues were sampled for cryosection, nuclei were stained with DAPI and analyzed by laser confocal microscopy. The Cy5.5-labeled antibody was mainly distributed in the vascular wall of the tumor tissue and tumor extracellular matrix (FIG. 5), and a large number of dispersed Cy5.5 fluorescent particles were observed in the cytoplasm. No apparent Cy5.5 labeled antibody was observed in the non-tumor tissues.

Example 7: Pharmacodynamic Effect of the Antibody in Animals

The amino acid sequence of the fusion protein of the DE2 antibody and interleukin-2 is set forth in SEQ NO: 74. After expressed by CHO-K1 cells and purified, it was used to experimentally verify that the DE2 antibody can improve the inhibition effect of interleukin-2 on tumor growth.

Healthy Bal b/c mice of approximately 20 g/mouse were injected axillary with $3 \times 10^6$ mouse teratoma cells F9, and after 6 days, the mice with a tumor volume of 70-100 mm$^3$ were selected for pharmacodynamic study. The tumor volume was calculated by: tumor maximal diameter (mm)× minimal diameter (mm)×minimal diameter (mm)×0.5. The relative tumor volume was calculated by: ratio of tumor volume 15 days after inoculation to tumor volume 6 days after inoculation.

The administration method: the experimental group was administered 30 μg of the antibody drug DE2-IL2 per mouse via tail vein injection on day 6 and day 10 after tumor cell inoculation. The positive control group was injected via tail vein with 10 μg of human interleukin-2 (hIL-2) per mouse on day 6 and day 10, respectively. The negative control group was injected with an equal volume of saline, i.e. 50 μl per mouse. There were 7 mice in each group.

Experimental results: 15 days after tumor cell inoculation, the relative tumor volume of the negative control group was 22.0±9.5, the relative tumor volume of the positive control group was 16.6±6.1, and the relative tumor volume of the experimental group was 5.7±4.0. The relative tumor volumes between the experimental group and the negative or the positive control group were statistically significant (p<0.01). There was no statistical difference in the relative tumor volumes between the negative and the positive control group.

The experiments showed that both hIL-2 and DE2-IL2 can inhibit the growth of mouse teratoma; and the DE2-IL2 is more remarkable than hIL-2 in the tumor inhibition effect, and slows down the growth speed of tumors obviously.

Example 8: Linear Epitope Analysis of High Affinity Antibodies

Polypeptides of varying lengths were synthesized according to the ED-B sequence, which generally consisted of 6-10 amino acids. Synthetic polypeptides were separately coupled to bovine serum albumin (BSA) with glutaraldehyde to form polypeptide-BSAs.

A proper amount of BSA was taken to be fully dissolved in 0.1 mol/L of boric acid buffer (pH=8.5), and a certain amount of a synthesized polypeptide was added proportionally and uniformly mixed. The binding ratio of the BSA molecule to the polypeptide molecule was 1:10. Then 1 mL of 0.3% glutaraldehyde in boric acid buffer was added slowly under shaking and left for 2 hours at room temperature. To neutralize glutaraldehyde that was not reacted completely, 0.25 mL of glycine was added to the above reaction solution, and continued for 30 min at room temperature for neutralization. Dialysis was performed with boric acid buffer for 24 hours, changing dialysate for 4 times and stored at −20° C. for use.

Different peptide-BSAs were diluted to the same concentration, coated on an ELISA plate respectively and the ED-B as positive control, left standstill at 37° C. for 2 hours. The plate was washed 3 times in PBS (pH=7.4), and then blocked with 5% skim milk powder at 37° C. for 1 hour. After washing 3 times in PBS, horseradish peroxidase-labeled DE2-Fc was added, incubating at 37° C. for 1 hour and the plate was washed 6 times in PBS. The substrate tetramethylbenzidine (TMB) of horseradish peroxidase was added, and the plate was left standstill at room temperature for 15 min in dark. 2 mol/L of sulfuric acid was added to stop the reaction. OD450 absorbance values were determined and the absorbance values of different polypeptide samples were compared. A high optical value indicates a greater binding to the DE2-Fc antibody.

Figures 5, 6:
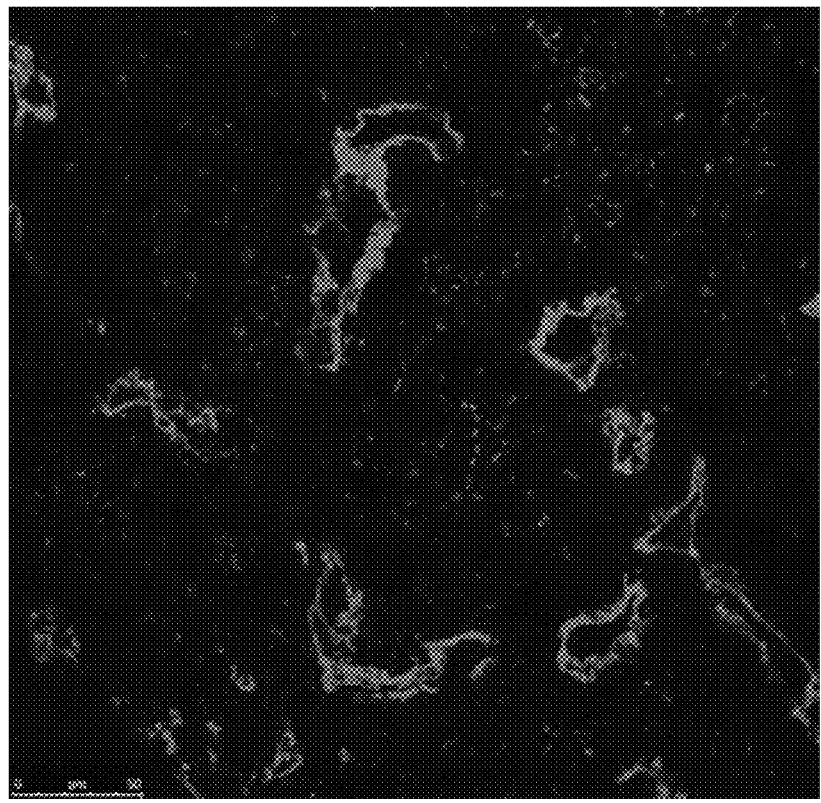
FIG. 5 shows the distribution of the DE2 antibody in solid tumor tissues. Tumor tissue cryosection analysis was performed 16 hours after Cy5.5-labeled DE2 antibody was injected intravenously into mice. Cy5.5-labeled antibodies were mainly distributed on blood vessels and tumor extracellular matrix.
FIG. 6 shows an epitope by which the DE2 antibody binds to ED-B. The synthetic polypeptide sequence is represented by horizontal lines, and the thickness of the lines indicates the relative affinity.
Figure 7:
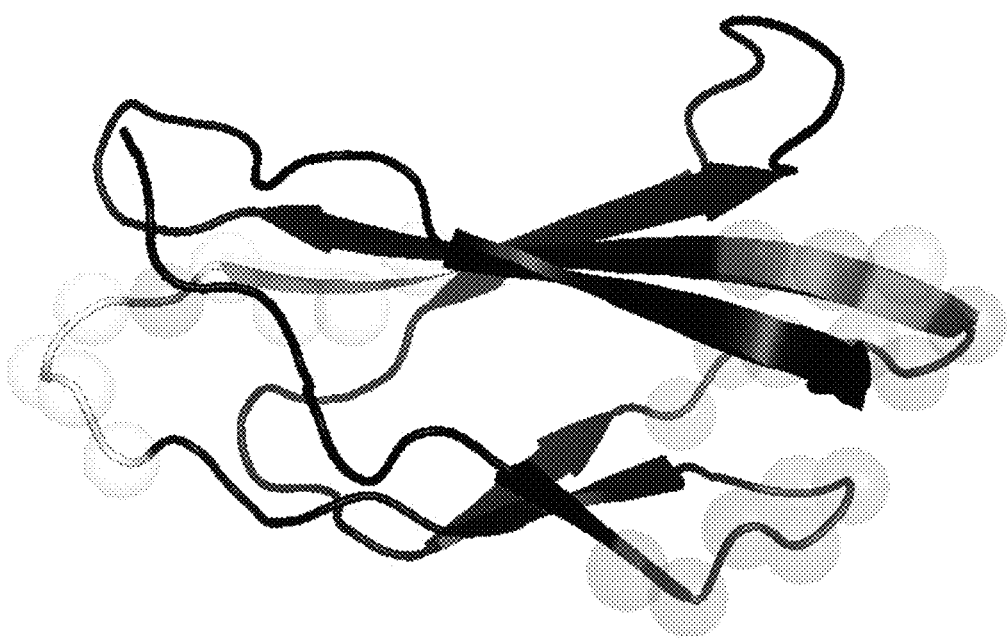
FIG. 7 shows an epitope by which the DE2 antibody binds to ED-B. The regions in the polypeptide with the highest binding capacity to the DE2 antibody are marked by light gray spheres and dark gray spheres.

The results were shown in the following table:

Based on the test results, antigenic epitope maps 6 and 7 were plotted. FIG. 6 shows an antigenic epitope by which the DE2 antibody binds to the ED-B. The synthetic polypeptide sequence is represented by horizontal lines, and the thickness of the lines indicates the relative affinity. FIG. 7 also shows the antigenic epitope by which the DE2 antibody binds to the ED-B, in which the region of the polypeptide with the highest binding capacity to the DE2 antibody is marked by a transparent circle.

The experimental results showed that the DE2 antibody can bind to a peptide fragment of the antigen ED-B, i.e., the DE2 can recognize a linear epitope of ED-B, suggesting that the DE2 can recognize and bind to the denatured ED-B protein or fragment. The linear epitope VDITDS (SEQ ID NO: 76) numbered EDB112, is one of the important regions recognized by the DE2 antibody; the linear epitope TGLEPGIDY (SEQ ID NO: 88) numbered EDB141, is one of the important regions recognized by the DE2 antibody; and the linear epitope NSSTIIGYR (SEQ ID NO: 81) numbered EDB121, is one of the important regions recognized by the DE2 antibody.

As shown in FIG. 7, the EDB 112, EDB 141 and EDB 121 are all in the irregular curled regions of the ED-B. The polypeptides EDB112 and EDB141 are spatially adjacent and have strong affinity for the DE2 antibody.

| Polypeptide No. | Positions of polypeptides in the antigen | Polypeptide sequence | SEQ ID NO: | The number of amino acids | Binding ability of the polypeptide to the antibody | Notes |
| --- | --- | --- | --- | --- | --- | --- |
| EDB111 | 11-19 | VDITDSSIG | 75 | 9 | + | |
| EDB112 | 11-16 | VDITDS | 76 | 6 | +++++ | Antigenic epitope |
| EDB113 | 12-17 | DITDSS | 77 | 6 | +++ | |
| EDB114 | 14-21 | TDSSIGLR | 78 | 8 | ++ | |
| EDB115 | 16-21 | SSIGLR | 79 | 6 | ++ | |
| EDB12 | 24-34 | PLNSSTIIGYR | 80 | 11 | | |
| EDB121 | 26-34 | NSSTIIGYR | 81 | 9 | +++++ | Antigenic epitope |
| EDB122 | 29-34 | TIIGYR | 82 | 6 | +++ | |
| EDB123 | 27-34 | SSTIIGYR | 83 | 8 | | |
| EDB124 | 28-34 | STIIGYR | 84 | 7 | | |
| EDB125 | 26-33 | NSSTIIGY | 85 | 8 | | |
| EDB126 | 26-32 | NSSTIIG | 86 | 7 | | |
| EDB14 | 60-70 | VTGLEPGIDYD | 87 | 11 | ++ | |
| EDB141 | 61-69 | TGLEPGIDY | 88 | 9 | ++++ | Antigenic epitope |
| EDB142 | 60-67 | VTGLEPGI | 89 | 8 | ++ | |
| EDB143 | 64-70 | EPGIDYD | 90 | 7 | + | |
| EDB144 | 62-69 | GLEPGIDY | 91 | 8 | | |
| EDB145 | 61-68 | TGLEPGID | 92 | 8 | | |
| EDB146 | 62-68 | GLEPGID | 93 | 7 | | |

The invention claimed is:

1. An isolated antibody or antigen-binding fragment thereof that specifically binds to an extra-domain B (ED-B) protein, wherein the isolated antibody or antigen-binding fragment comprises a light chain variable region (VL) and a heavy chain variable region (VH), wherein:
   (i) the heavy chain variable region comprises:
      a VH CDR1 comprising an amino acid sequence as set forth in SEQ ID NO: 5,
      a VH CDR2 comprising an amino acid sequence as set forth in SEQ ID NO: 6, and
      a VH CDR3 comprising an amino acid sequence as set forth in SEQ ID NO: 7; and
      the light chain variable region comprises:
      a VL CDR1 comprising an amino acid sequence as set forth in SEQ ID NO: 114,
      a VL CDR2 comprising an amino acid sequence as set forth in SEQ ID NO: 138, and
      a VL CDR3 comprising an amino acid sequence as set forth in SEQ ID NO: 10; or
   (ii) the heavy chain variable region comprises:
      a VH CDR1 comprising an amino acid sequence as set forth in SEQ ID NO: 5,
      a VH CDR2 comprising an amino acid sequence as set forth in SEQ ID NO: 6, and
      a VH CDR3 comprising an amino acid sequence as set forth in SEQ ID NO: 7; and
      the light chain variable region comprises:
      a VL CDR1 comprising an amino acid sequence as set forth in SEQ ID NO: 143,
      a VL CDR2 comprising an amino acid sequence as set forth in SEQ ID NO: 144, and
      a VL CDR3 comprising an amino acid sequence as set forth in SEQ ID NO: 10.

2. The isolated antibody or antigen-binding fragment of claim 1, wherein the antibody or antigen-binding fragment has an equilibrium binding dissociation constant (KD) of $1\times10^{-8}$ M or less, $1\times10^{6-9}$ M or less, or $1\times10^{-10}$ M or less.

3. The isolated antibody or antigen-binding fragment of claim 1, wherein the antibody or antigen-binding fragment is selected from the group consisting of a single-chain antibody, a double-chain antibody, a triple-chain antibody, a minibody, a synthetic antibody, a recombinantly produced antibody, a multispecific antibody, a bispecific antibody, a human antibody, a chimeric antibody, an Fab fragment, an Fab' fragment, an $F(ab')_2$ fragment, an Fv fragment, a disulfide bond-ligated Fv (dsFv), an Fd fragment, an Fd' fragment, a single-chain Fv (scFv), a single-chain Fab (scFab), and a diabody, optionally the antibody is a human immunoglobulin IgG.

4. The isolated antibody or antigen-binding fragment of claim 1, which comprises the amino acid sequence as set forth in SEQ ID NO: 14 or SEQ ID NO: 146.

5. A pharmaceutical composition comprising the isolated antibody or antigen-binding fragment of claim 1 and a pharmaceutically acceptable carrier.

6. The pharmaceutical composition of claim 5, wherein the pharmaceutical composition comprises a fusion protein, a radioisotope, a fluorescent dye, a chemical and/or a nanoparticle.

7. A method of diagnosing or treating a tumor or cancer expressing FN(B+) containing ED-B domain in a subject, comprising administrating the subject an effective amount of the isolated antibody or antigen-binding fragment of claim 1.

8. The method of claim 7, wherein the tumor or cancer is selected from the group consisting of teratoma, nasopharyngeal carcinoma, head and neck cancer, esophageal cancer, gastric cancer, colorectal cancer, lung cancer, breast cancer and soft tissue sarcoma.

9. A method of diagnosing or treating a tumor or cancer expressing FN(B+) containing ED-B domain in a subject, comprising administrating the subject an effective amount of the pharmaceutical composition of claim 5.

10. The method of claim 9, wherein the tumor or cancer is selected from the group consisting of teratoma, nasopharyngeal carcinoma, head and neck cancer, esophageal cancer, gastric cancer, colorectal cancer, lung cancer, breast cancer and soft tissue sarcoma.

11. A kit comprising the isolated antibody or antigen-binding fragment of claim 1, suitable for using in: (i) diagnosing in vivo distribution of a tumor tissue or a pathological tissue section expressing fibronectin comprising ED-B protein domain, (ii) analyzing and characterizing a cell or a protein containing an ED-B protein domain, or (iii) affinity purifying a cell or a protein molecule containing an ED-B protein domain.

12. A method of analyzing and characterizing a cell or a protein or affinity purifying a cell or a protein molecule containing an ED-B protein domain, comprising contacting the cell or the protein with the isolated antibody or antigen-binding fragment of claim 1.

* * * * *

SEQUENCE LISTING

<160> NUMBER OF SEQ ID NOS: 147

<210> SEQ ID NO 1
<211> LENGTH: 116
<212> TYPE: PRT
<213> ORGANISM: Artificial Sequence
<220> FEATURE:
<223> OTHER INFORMATION: VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Met Ser Tyr Phe Asp Tyr Trp Gly Gln Gly Thr Leu Val
            100                 105                 110

Thr Val Ser Ser
        115

<210> SEQ ID NO 2
<211> LENGTH: 348
<212> TYPE: DNA
<213> ORGANISM: Artificial Sequence
<220> FEATURE:
<223> OTHER INFORMATION: DNA coding for VH

<400> SEQUENCE: 2
gaagtgcagc tgttggaatc tggggggtggc ttggtacagc ctgggggtc cctgcgtctc     60 tcctgtgcag ccagcggctt caccttagt agctatgcca tgagctgggt ccgccaggct    120
ccagggaaag gcctggaatg ggtcagtcgt attagtccga gtggcagcag tacatactac    180
gcagactccg tgaaaggtcg cttcaccatc tcccgtgaca attccaaaaa cacgctgtat    240
ctgcaaatga acagcctgcg tgccgaagac accgccgtat attactgtgc gcgtaggatg    300
agttatttcg attactgggg ccagggcacc ctggtcaccg tctccagt                 348

<210> SEQ ID NO 3
<211> LENGTH: 110
<212> TYPE: PRT
<213> ORGANISM: Artificial Sequence
<220> FEATURE:
<223> OTHER INFORMATION: VL

<400> SEQUENCE: 3

Gln Ser Ala Leu Thr Gln Pro Ala Ser Val Ser Gly Ser Pro Gly Gln
1               5                   10                  15

Ser Ile Thr Ile Ser Cys Ser Gly Asp Ser Leu Gly Ile Phe Arg Ser
            20                  25                  30

Gly Met Val Ser Trp Tyr Gln Gln His Pro Gly Lys Ala Pro Lys Leu
        35                  40                  45

Met Ile Tyr Leu Pro Thr Ser Arg Pro Ser Gly Val Ser Asn Arg Phe
    50                  55                  60

```
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Trp Asp Gly Arg
                 85                  90                  95

Gln Pro Val Phe Gly Gly Gly Thr Lys Leu Thr Val Leu Gly
            100                 105                 110

<210> SEQ ID NO 4
<211> LENGTH: 330
<212> TYPE: DNA
<213> ORGANISM: Artificial Sequence
<220> FEATURE:
<223> OTHER INFORMATION: DNA coding for VL

<400> SEQUENCE: 4
cagtctgccc tgactcagcc tgcctccgtg tctgggtctc ctggccagtc gatcaccatc       60
tcctgcagcg gtgatagcct gggtattttt cggtctggta tggtctcctg gtaccaacag      120
cacccaggca agccccccaa actcatgatt tatcttccta cgtcgcgccc ctcaggcgtt      180
tctaaccggt tctctggctc caagtctggc aacacggcct ccctgaccat ctctggtctc      240
caggctgagg acgaggctga ttattactgc cagtcatggg atgggcggca gccggtcttc      300
ggcggtggca ctaaactgac tgtgctgggt                                        330

<210> SEQ ID NO 5
<211> LENGTH: 5
<212> TYPE: PRT
<213> ORGANISM: Artificial Sequence
<220> FEATURE:
<223> OTHER INFORMATION: HCDR1

<400> SEQUENCE: 5

Ser Tyr Ala Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: HCDR2

<400> SEQUENCE: 6

Arg Ile Ser Pro Ser Gly Ser Ser Thr Tyr Tyr Ala Asp Ser Val Lys
1               5                   10                  15

Gly

<210> SEQ ID NO 7
<211> LENGTH: 7
<212> TYPE: PRT
<213> ORGANISM: Artificial Sequence
<220> FEATURE:
<223> OTHER INFORMATION: HCDR3

<400> SEQUENCE: 7

Arg Met Ser Tyr Phe Asp Tyr
1               5

<210> SEQ ID NO 8
<211> LENGTH: 14
<212> TYPE: PRT
<213> ORGANISM: Artificial Sequence
<220> FEATURE:
```

```
<223> OTHER INFORMATION: LCDR1

<400> SEQUENCE: 8

Ser Gly Asp Ser Leu Gly Ile Phe Arg Ser Gly Met Val Ser
1               5                   10

<210> SEQ ID NO 9
<211> LENGTH: 7
<212> TYPE: PRT
<213> ORGANISM: Artificial Sequence
<220> FEATURE:
<223> OTHER INFORMATION: LCDR2

<400> SEQUENCE: 9

Leu Pro Thr Ser Arg Pro Ser
1               5

<210> SEQ ID NO 10
<211> LENGTH: 8
<212> TYPE: PRT
<213> ORGANISM: Artificial Sequence
<220> FEATURE:
<223> OTHER INFORMATION: LCDR3

<400> SEQUENCE: 10

Gln Ser Trp Asp Gly Arg Gln Pro
1               5

<210> SEQ ID NO 11
<211> LENGTH: 16
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Ser Gly Gly Gly Gly Ser Ser
1               5                   10                  15

<210> SEQ ID NO 12
<211> LENGTH: 48
<212> TYPE: DNA
<213> ORGANISM: Artificial Sequence
<220> FEATURE:
<223> OTHER INFORMATION: DNA coding for linker

<400> SEQUENCE: 12
ggtggtggcg gttcaggcgg tggtggctct ggtggcggtg ggtccagc                48

<210> SEQ ID NO 13
<211> LENGTH: 477
<212> TYPE: PRT
<213> ORGANISM: Artificial Sequence
<220> FEATURE:
<223> OTHER INFORMATION: DE2-Fc

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Met Ser Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Gln Ser Ala Leu Thr Gln Pro Ala Ser Val Ser Gly
        130                 135                 140

Ser Pro Gly Gln Ser Ile Thr Ile Ser Cys Ser Gly Asp Ser Leu Gly
145                 150                 155                 160

Ile Phe Arg Ser Gly Met Val Ser Trp Tyr Gln Gln His Pro Gly Lys
            165                 170                 175

Ala Pro Lys Leu Met Ile Tyr Leu Pro Thr Ser Arg Pro Ser Gly Val
        180                 185                 190

Ser Asn Arg Phe Ser Gly Ser Lys Ser Gly Asn Thr Ala Ser Leu Thr
        195                 200                 205

Ile Ser Gly Leu Gln Ala Glu Asp Glu Ala Asp Tyr Tyr Cys Gln Ser
210                 215                 220

Trp Asp Gly Arg Gln Pro Val Phe Gly Gly Gly Thr Lys Leu Thr Val
225                 230                 235                 240

Leu Gly Ala Ala Ala Glu Pro Lys Ser Cys Asp Lys Thr His Thr Cys
            245                 250                 255

Pro Pro Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
        340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
        370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
        420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys
465                 470                 475
```

<210> SEQ ID NO 14
<211> LENGTH: 242
<212> TYPE: PRT
<213> ORGANISM: Artificial Sequence
<220> FEATURE:
<223> OTHER INFORMATION: A11

<400> SEQUENCE: 14

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Met Ser Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Gln Ser Ala Leu Thr Gln Pro Ala Ser Val Ser Gly
    130                 135                 140

Ser Pro Gly Gln Ser Ile Thr Ile Ser Cys Ser Gly Asp Ser Leu Gly
145                 150                 155                 160

Ile Gly Ser Asn Asn Tyr Val Ser Trp Tyr Gln Gln His Pro Gly Lys
                165                 170                 175

Ala Pro Lys Leu Met Ile Tyr Asp Asp Asn Lys Arg Pro Ser Gly Val
            180                 185                 190

Ser Asn Arg Phe Ser Gly Ser Lys Ser Gly Asn Thr Ala Ser Leu Thr
        195                 200                 205

Ile Ser Gly Leu Gln Ala Glu Asp Glu Ala Asp Tyr Tyr Cys Gln Ser
    210                 215                 220

Trp Asp Gly Arg Gln Pro Val Phe Gly Gly Gly Thr Lys Leu Thr Val
225                 230                 235                 240

Leu Gly
```

<210> SEQ ID NO 15
<211> LENGTH: 726
<212> TYPE: DNA
<213> ORGANISM: Artificial Sequence
<220> FEATURE:
<223> OTHER INFORMATION: DNA coding for A11

<400> SEQUENCE: 15

```
gaagtgcagc tgttggaatc tgggggtggc ttggtacagc ctggggggtc cctgcgtctc      60
tcctgtgcag ccagcggctt cacctttagt agctatgcca tgagctgggt ccgccaggct     120
ccagggaaag gcctggaatg ggtcagtcgt attagtccga gtggcagcag tacatactac     180
gcagactccg tgaaaggtcg cttcaccatc tcccgtgaca attccaaaaa cacgctgtat     240
ctgcaaatga acagcctgcg tgccgaagac accgccgtat attactgtgc gcgtaggatg     300
agttatttcg attactgggg ccagggcacc ctggtcaccg tctccagtgg tggtggcggt     360
```

```
tcaggcggtg gtggctctgg tggcggtggg tccagccagt ctgccctgac tcagcctgcc    420
tccgtgtctg gtctcctgg ccagtcgatc accatctcct gcagcggtga tagcctgggt     480
attggttcca ataactatgt ctcctggtac aacagcacc caggcaaagc ccccaaactc     540
atgatttatg acgataataa acgccccctca ggcgtttcta accggttctc tggctccaag   600
tctggcaaca cggcctccct gaccatctct ggtctccagg ctgaggacga ggctgattat    660
tactgccagt catgggatgg cggcagccg gtcttcggcg gtggcactaa actgactgtg     720
ctgggt                                                               726
```

\<210\> SEQ ID NO 16
\<211\> LENGTH: 91
\<212\> TYPE: PRT
\<213\> ORGANISM: Homo sapiens

\<400\> SEQUENCE: 16

```
Glu Val Pro Gln Leu Thr Asp Leu Ser Phe Val Asp Ile Thr Asp Ser
1               5                   10                  15

Ser Ile Gly Leu Arg Trp Thr Pro Leu Asn Ser Ser Thr Ile Ile Gly
            20                  25                  30

Tyr Arg Ile Thr Val Val Ala Ala Gly Glu Gly Ile Pro Ile Phe Glu
        35                  40                  45

Asp Phe Val Asp Ser Ser Val Gly Tyr Tyr Thr Val Thr Gly Leu Glu
    50                  55                  60

Pro Gly Ile Asp Tyr Asp Ile Ser Val Ile Thr Leu Ile Asn Gly Gly
65                  70                  75                  80

Glu Ser Ala Pro Thr Thr Leu Thr Gln Gln Thr
                85                  90
```

\<210\> SEQ ID NO 17
\<211\> LENGTH: 25
\<212\> TYPE: DNA
\<213\> ORGANISM: Artificial Sequence
\<220\> FEATURE:
\<223\> OTHER INFORMATION: primer

\<400\> SEQUENCE: 17

```
ggcgaattcc gaagtgcagc tgttg                                           25
```

\<210\> SEQ ID NO 18
\<211\> LENGTH: 56
\<212\> TYPE: DNA
\<213\> ORGANISM: Artificial Sequence
\<220\> FEATURE:
\<223\> OTHER INFORMATION: primer
\<220\> FEATURE:
\<221\> NAME/KEY: misc_feature
\<222\> LOCATION: (23)..(23)
\<223\> OTHER INFORMATION: m is a, or c
\<220\> FEATURE:
\<221\> NAME/KEY: misc_feature
\<222\> LOCATION: (24)..(25)
\<223\> OTHER INFORMATION: n is a, c, g, or t
\<220\> FEATURE:
\<221\> NAME/KEY: misc_feature
\<222\> LOCATION: (26)..(26)
\<223\> OTHER INFORMATION: m is a, or c
\<220\> FEATURE:
\<221\> NAME/KEY: misc_feature
\<222\> LOCATION: (27)..(28)
\<223\> OTHER INFORMATION: n is a, c, g, or t
\<220\> FEATURE:
\<221\> NAME/KEY: misc_feature
\<222\> LOCATION: (29)..(29)
\<223\> OTHER INFORMATION: m is a, or c <220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: m is a, or c
<220> FEATURE:
<221> NAME/KEY: misc_feature
<222> LOCATION: (33)..(34)
<223> OTHER INFORMATION: n is a, c, g, or t

<400> SEQUENCE: 18
tgccctggcc ccagtaatcg aamnnmnnmn nmnnacgcgc acagtaatat acggcg    56

<210> SEQ ID NO 19
<211> LENGTH: 30
<212> TYPE: DNA
<213> ORGANISM: Artificial Sequence
<220> FEATURE:
<223> OTHER INFORMATION: primer

<400> SEQUENCE: 19
ttcgattact ggggccaggg caccctggtc    30

<210> SEQ ID NO 20
<211> LENGTH: 60
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (22)..(22)
<223> OTHER INFORMATION: m is a, or c
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: m is a, or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: m is a, or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: m is a, or c
<220> FEATURE:
<221> NAME/KEY: misc_feature
<222> LOCATION: (32)..(33)
<223> OTHER INFORMATION: n is a, c, g, or t

<400> SEQUENCE: 20
tttagtgcca ccgccgaaga cmnnmnnmnn mnnatcccat gactggcagt aataatcagc    60

<210> SEQ ID NO 21
<211> LENGTH: 52
<212> TYPE: DNA
<213> ORGANISM: Artificial Sequence
<220> FEATURE:

<223> OTHER INFORMATION: primer

<400> SEQUENCE: 21
ataagaatgc ggccgcaccc agcacagtca gtttagtgcc accgccgaag ac         52

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
atcaccatct cctgcagcgg tgatagcctg ggtatt                           36

<210> SEQ ID NO 23
<211> LENGTH: 59
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (25)..(25)
<223> OTHER INFORMATION: k is t, or g
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: k is t, or g
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: k is t, or g
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: k is t, or g
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: k is t, or g

<400> SEQUENCE: 23
cagcggtgat agcctgggta ttnnknnknn knnknnkgtc tcctggtacc aacagcacc   59

<210> SEQ ID NO 24
<211> LENGTH: 56
<212> TYPE: DNA
<213> ORGANISM: Artificial Sequence
<220> FEATURE:
<223> OTHER INFORMATION: primer
<220> FEATURE:
<221> NAME/KEY: misc_feature

```
<222> LOCATION: (23)..(23)
<223> OTHER INFORMATION: m is a, or c
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (26)..(26)
<223> OTHER INFORMATION: m is a, or c
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: m is a, or c
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: m is a, or c
<220> FEATURE:
<221> NAME/KEY: misc_feature
<222> LOCATION: (33)..(34)
<223> OTHER INFORMATION: n is a, c, g, or t

<400> SEQUENCE: 24
ggttagaaac gcctgagggg cgmnnmnnmn nmnnataaat catgagtttg ggggct        56

<210> SEQ ID NO 25
<211> LENGTH: 38
<212> TYPE: DNA
<213> ORGANISM: Artificial Sequence
<220> FEATURE:
<223> OTHER INFORMATION: primer

<400> SEQUENCE: 25
ttggagccag agaaccggtt agaaacgcct gaggggcg        38

<210> SEQ ID NO 26
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 26

Ala Trp Ser Ser Ala
1               5

<210> SEQ ID NO 27
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 27

Phe Arg Ser Gly Met
1               5

<210> SEQ ID NO 28
<211> LENGTH: 5
<212> TYPE: PRT
<213> ORGANISM: Artificial Sequence
<220> FEATURE:
```

<223> OTHER INFORMATION: LCDR mutated residues

<400> SEQUENCE: 28

Arg Ala Phe Thr Pro
1               5

<210> SEQ ID NO 29
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 29

Arg Leu Pro Pro Gly
1               5

<210> SEQ ID NO 30
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 30

Ser Arg Ser Thr Tyr
1               5

<210> SEQ ID NO 31
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 31

Pro Gly Phe Ser Pro
1               5

<210> SEQ ID NO 32
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 32

His Met Pro Pro Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 33

Leu Ala Arg Ser Pro
1               5

<210> SEQ ID NO 34
<211> LENGTH: 5
<212> TYPE: PRT
<213> ORGANISM: Artificial Sequence
<220> FEATURE:
<223> OTHER INFORMATION: LCDR mutated residues

```
<400> SEQUENCE: 34

Leu Trp Leu Ser Pro
1               5

<210> SEQ ID NO 35
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 35

Ala Trp Ser Ser Ser
1               5

<210> SEQ ID NO 36
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 36

Cys Pro Leu Val Ser
1               5

<210> SEQ ID NO 37
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 37

Phe Leu Pro Gly Arg
1               5

<210> SEQ ID NO 38
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 38

Gly Trp Ser Gly Ser
1               5

<210> SEQ ID NO 39
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 39

Leu Gly Ser Gly Pro
1               5

<210> SEQ ID NO 40
<211> LENGTH: 5
<212> TYPE: PRT
<213> ORGANISM: Artificial Sequence
<220> FEATURE:
<223> OTHER INFORMATION: LCDR mutated residues
```

```
<400> SEQUENCE: 40

Leu Arg Pro Ala Pro
1               5

<210> SEQ ID NO 41
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 41

Pro Ala Arg Ser Pro
1               5

<210> SEQ ID NO 42
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 42

Pro Ser Phe Ser Pro
1               5

<210> SEQ ID NO 43
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 43

Pro Trp Val Ser Gly
1               5

<210> SEQ ID NO 44
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 44

Arg Leu Phe Leu Pro
1               5

<210> SEQ ID NO 45
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 45

Ser Arg Ser Arg Tyr
1               5

<210> SEQ ID NO 46
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 46
```

Ser Arg Ser Thr Tyr
1               5

<210> SEQ ID NO 47
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 47

Thr Gln Ser Lys Tyr
1               5

<210> SEQ ID NO 48
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 48

Val Arg Ser Leu Gly
1               5

<210> SEQ ID NO 49
<211> LENGTH: 5
<212> TYPE: PRT
<213> ORGANISM: Artificial Sequence
<220> FEATURE:
<223> OTHER INFORMATION: LCDR mutated residues

<400> SEQUENCE: 49

Trp Leu Cys Gly Pro
1               5

<210> SEQ ID NO 50
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 50

Ser Ala Ser Glu
1

<210> SEQ ID NO 51
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 51

Leu Pro Thr Ser
1

<210> SEQ ID NO 52
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 52

Gln Ser His Trp
1

<210> SEQ ID NO 53
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 53

Ser Asn Thr Thr
1

<210> SEQ ID NO 54
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 54

Ser Ala Glu Leu
1

<210> SEQ ID NO 55
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 55

Ser Tyr Arg Ser
1

<210> SEQ ID NO 56
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 56

Ser Ser Gln His
1

<210> SEQ ID NO 57
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 57

Ser His Gly Arg
1

<210> SEQ ID NO 58
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 58

Trp Ser Asn Asp

```
<210> SEQ ID NO 59
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 59

Phe Arg Val Ser
1

<210> SEQ ID NO 60
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 60

Ser Ala Tyr Leu
1

<210> SEQ ID NO 61
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 61

Asp Leu Met Ser
1

<210> SEQ ID NO 62
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 62

Leu Lys Ser Gln
1

<210> SEQ ID NO 63
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 63

Leu Pro Thr Phe
1

<210> SEQ ID NO 64
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 64

Ala Asn Glu Leu
1
```

<210> SEQ ID NO 65
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 65

Pro Arg Thr Pro
1

<210> SEQ ID NO 66
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 66

Pro Asn Ala Arg
1

<210> SEQ ID NO 67
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 67

Pro Ser Asp His
1

<210> SEQ ID NO 68
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 68

Ala Ser Gln Ser
1

<210> SEQ ID NO 69
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 69

Ser Ala Glu Leu
1

<210> SEQ ID NO 70
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 70

Ser Ala Lys Leu
1

<210> SEQ ID NO 71
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 71

Ser Ala Glu Leu
1

<210> SEQ ID NO 72
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 72

Leu Asn Gly Arg
1

<210> SEQ ID NO 73
<211> LENGTH: 4
<212> TYPE: PRT
<213> ORGANISM: Artificial Sequence
<220> FEATURE:
<223> OTHER INFORMATION: LCDR mutated residues

<400> SEQUENCE: 73

Leu Pro Arg Ser
1

<210> SEQ ID NO 74
<211> LENGTH: 383
<212> TYPE: PRT
<213> ORGANISM: Artificial Sequence
<220> FEATURE:
<223> OTHER INFORMATION: DE2-IL-2 fusion

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Met Ser Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Gln Ser Ala Leu Thr Gln Pro Ala Ser Val Ser Gly Ser
    130                 135                 140

Pro Gly Gln Ser Ile Thr Ile Ser Cys Ser Gly Asp Ser Leu Gly Ile
145                 150                 155                 160

```
Phe Arg Ser Gly Met Val Ser Trp Tyr Gln Gln His Pro Gly Lys Ala
                165                 170                 175

Pro Lys Leu Met Ile Tyr Leu Pro Thr Ser Arg Pro Ser Gly Val Ser
            180                 185                 190

Asn Arg Phe Ser Gly Ser Lys Ser Gly Asn Thr Ala Ser Leu Thr Ile
        195                 200                 205

Ser Gly Leu Gln Ala Glu Asp Glu Ala Asp Tyr Tyr Cys Gln Ser Trp
    210                 215                 220

Asp Gly Arg Gln Pro Val Phe Gly Gly Gly Thr Lys Leu Thr Val Leu
225                 230                 235                 240

Gly Gly Gly Gly Ser Gly Gly Gly Gly Ser Ala Pro Thr Ser Ser Ser
                245                 250                 255

Thr Lys Lys Thr Gln Leu Gln Leu Glu His Leu Leu Leu Asp Leu Gln
                260                 265                 270

Met Ile Leu Asn Gly Ile Asn Asn Tyr Lys Asn Pro Lys Leu Thr Arg
            275                 280                 285

Met Leu Thr Phe Lys Phe Tyr Met Pro Lys Lys Ala Thr Glu Leu Lys
        290                 295                 300

His Leu Gln Cys Leu Glu Glu Glu Leu Lys Pro Leu Glu Glu Val Leu
305                 310                 315                 320

Asn Leu Ala Gln Ser Lys Asn Phe His Leu Arg Pro Arg Asp Leu Ile
                325                 330                 335

Ser Asn Ile Asn Val Ile Val Leu Glu Leu Lys Gly Ser Glu Thr Thr
            340                 345                 350

Phe Met Cys Glu Tyr Ala Asp Glu Thr Ala Thr Ile Val Glu Phe Leu
        355                 360                 365

Asn Arg Trp Ile Thr Phe Cys Gln Ser Ile Ile Ser Thr Leu Thr
    370                 375                 380

<210> SEQ ID NO 75
<211> LENGTH: 9
<212> TYPE: PRT
<213> ORGANISM: Artificial Sequence
<220> FEATURE:
<223> OTHER INFORMATION: EDB111

<400> SEQUENCE: 75

Val Asp Ile Thr Asp Ser Ser Ile Gly
1               5

<210> SEQ ID NO 76
<211> LENGTH: 6
<212> TYPE: PRT
<213> ORGANISM: Artificial Sequence
<220> FEATURE:
<223> OTHER INFORMATION: EDB112

<400> SEQUENCE: 76

Val Asp Ile Thr Asp Ser
1               5

<210> SEQ ID NO 77
<211> LENGTH: 6
<212> TYPE: PRT
<213> ORGANISM: Artificial Sequence
<220> FEATURE:
<223> OTHER INFORMATION: EDB113

<400> SEQUENCE: 77

Asp Ile Thr Asp Ser Ser
```

```
1               5
```

<210> SEQ ID NO 78
<211> LENGTH: 8
<212> TYPE: PRT
<213> ORGANISM: Artificial Sequence
<220> FEATURE:
<223> OTHER INFORMATION: EDB114

<400> SEQUENCE: 78

```
Thr Asp Ser Ser Ile Gly Leu Arg
1               5
```

<210> SEQ ID NO 79
<211> LENGTH: 6
<212> TYPE: PRT
<213> ORGANISM: Artificial Sequence
<220> FEATURE:
<223> OTHER INFORMATION: EDB115

<400> SEQUENCE: 79

```
Ser Ser Ile Gly Leu Arg
1               5
```

<210> SEQ ID NO 80
<211> LENGTH: 11
<212> TYPE: PRT
<213> ORGANISM: Artificial Sequence
<220> FEATURE:
<223> OTHER INFORMATION: EDB12

<400> SEQUENCE: 80

```
Pro Leu Asn Ser Ser Thr Ile Ile Gly Tyr Arg
1               5                   10
```

<210> SEQ ID NO 81
<211> LENGTH: 9
<212> TYPE: PRT
<213> ORGANISM: Artificial Sequence
<220> FEATURE:
<223> OTHER INFORMATION: EDB121

<400> SEQUENCE: 81

```
Asn Ser Ser Thr Ile Ile Gly Tyr Arg
1               5
```

<210> SEQ ID NO 82
<211> LENGTH: 6
<212> TYPE: PRT
<213> ORGANISM: Artificial Sequence
<220> FEATURE:
<223> OTHER INFORMATION: EDB122

<400> SEQUENCE: 82

```
Thr Ile Ile Gly Tyr Arg
1               5
```

<210> SEQ ID NO 83
<211> LENGTH: 8
<212> TYPE: PRT
<213> ORGANISM: Artificial Sequence
<220> FEATURE:
<223> OTHER INFORMATION: EDB123

<400> SEQUENCE: 83

```
Ser Ser Thr Ile Ile Gly Tyr Arg
1               5
```

```
<210> SEQ ID NO 84
<211> LENGTH: 7
<212> TYPE: PRT
<213> ORGANISM: Artificial Sequence
<220> FEATURE:
<223> OTHER INFORMATION: EDB124

<400> SEQUENCE: 84

Ser Thr Ile Ile Gly Tyr Arg
1               5

<210> SEQ ID NO 85
<211> LENGTH: 8
<212> TYPE: PRT
<213> ORGANISM: Artificial Sequence
<220> FEATURE:
<223> OTHER INFORMATION: EDB125

<400> SEQUENCE: 85

Asn Ser Ser Thr Ile Ile Gly Tyr
1               5

<210> SEQ ID NO 86
<211> LENGTH: 7
<212> TYPE: PRT
<213> ORGANISM: Artificial Sequence
<220> FEATURE:
<223> OTHER INFORMATION: EDB126

<400> SEQUENCE: 86

Asn Ser Ser Thr Ile Ile Gly
1               5

<210> SEQ ID NO 87
<211> LENGTH: 11
<212> TYPE: PRT
<213> ORGANISM: Artificial Sequence
<220> FEATURE:
<223> OTHER INFORMATION: EDB14

<400> SEQUENCE: 87

Val Thr Gly Leu Glu Pro Gly Ile Asp Tyr Asp
1               5                   10

<210> SEQ ID NO 88
<211> LENGTH: 9
<212> TYPE: PRT
<213> ORGANISM: Artificial Sequence
<220> FEATURE:
<223> OTHER INFORMATION: EDB141

<400> SEQUENCE: 88

Thr Gly Leu Glu Pro Gly Ile Asp Tyr
1               5

<210> SEQ ID NO 89
<211> LENGTH: 8
<212> TYPE: PRT
<213> ORGANISM: Artificial Sequence
<220> FEATURE:
<223> OTHER INFORMATION: EDB142

<400> SEQUENCE: 89

Val Thr Gly Leu Glu Pro Gly Ile
1               5
```

```
<210> SEQ ID NO 90
<211> LENGTH: 7
<212> TYPE: PRT
<213> ORGANISM: Artificial Sequence
<220> FEATURE:
<223> OTHER INFORMATION: EDB143

<400> SEQUENCE: 90

Glu Pro Gly Ile Asp Tyr Asp
1               5

<210> SEQ ID NO 91
<211> LENGTH: 8
<212> TYPE: PRT
<213> ORGANISM: Artificial Sequence
<220> FEATURE:
<223> OTHER INFORMATION: EDB144

<400> SEQUENCE: 91

Gly Leu Glu Pro Gly Ile Asp Tyr
1               5

<210> SEQ ID NO 92
<211> LENGTH: 8
<212> TYPE: PRT
<213> ORGANISM: Artificial Sequence
<220> FEATURE:
<223> OTHER INFORMATION: EDB145

<400> SEQUENCE: 92

Thr Gly Leu Glu Pro Gly Ile Asp
1               5

<210> SEQ ID NO 93
<211> LENGTH: 7
<212> TYPE: PRT
<213> ORGANISM: Artificial Sequence
<220> FEATURE:
<223> OTHER INFORMATION: EDB146

<400> SEQUENCE: 93

Gly Leu Glu Pro Gly Ile Asp
1               5

<210> SEQ ID NO 94
<211> LENGTH: 15
<212> TYPE: PRT
<213> ORGANISM: Artificial Sequence
<220> FEATURE:
<223> OTHER INFORMATION: Linker

<400> SEQUENCE: 94

Gly Gly Gly Gly Ser Gly Gly Gly Gly Ser Gly Gly Gly Gly Ser
1               5                   10                  15

<210> SEQ ID NO 95
<211> LENGTH: 14
<212> TYPE: PRT
<213> ORGANISM: Artificial Sequence
<220> FEATURE:
<223> OTHER INFORMATION: LCDR1

<400> SEQUENCE: 95

Ser Gly Asp Ser Leu Gly Ile Ala Trp Ser Ser Ala Val Ser
1               5                   10
```

```
<210> SEQ ID NO 96
<211> LENGTH: 14
<212> TYPE: PRT
<213> ORGANISM: Artificial Sequence
<220> FEATURE:
<223> OTHER INFORMATION: LCDR1

<400> SEQUENCE: 96

Ser Gly Asp Ser Leu Gly Ile Phe Arg Ser Gly Met Val Ser
1               5                   10

<210> SEQ ID NO 97
<211> LENGTH: 14
<212> TYPE: PRT
<213> ORGANISM: Artificial Sequence
<220> FEATURE:
<223> OTHER INFORMATION: LCDR1

<400> SEQUENCE: 97

Ser Gly Asp Ser Leu Gly Ile Arg Ala Phe Thr Pro Val Ser
1               5                   10

<210> SEQ ID NO 98
<211> LENGTH: 14
<212> TYPE: PRT
<213> ORGANISM: Artificial Sequence
<220> FEATURE:
<223> OTHER INFORMATION: LCDR1

<400> SEQUENCE: 98

Ser Gly Asp Ser Leu Gly Ile Arg Leu Pro Pro Gly Val Ser
1               5                   10

<210> SEQ ID NO 99
<211> LENGTH: 14
<212> TYPE: PRT
<213> ORGANISM: Artificial Sequence
<220> FEATURE:
<223> OTHER INFORMATION: LCDR1

<400> SEQUENCE: 99

Ser Gly Asp Ser Leu Gly Ile Ser Arg Ser Thr Tyr Val Ser
1               5                   10

<210> SEQ ID NO 100
<211> LENGTH: 14
<212> TYPE: PRT
<213> ORGANISM: Artificial Sequence
<220> FEATURE:
<223> OTHER INFORMATION: LCDR1

<400> SEQUENCE: 100

Ser Gly Asp Ser Leu Gly Ile Pro Gly Phe Ser Pro Val Ser
1               5                   10

<210> SEQ ID NO 101
<211> LENGTH: 14
<212> TYPE: PRT
<213> ORGANISM: Artificial Sequence
<220> FEATURE:
<223> OTHER INFORMATION: LCDR1

<400> SEQUENCE: 101

Ser Gly Asp Ser Leu Gly Ile His Met Pro Pro Tyr Val Ser
1               5                   10

<210> SEQ ID NO 102
```

```
<211> LENGTH: 14
<212> TYPE: PRT
<213> ORGANISM: Artificial Sequence
<220> FEATURE:
<223> OTHER INFORMATION: LCDR1

<400> SEQUENCE: 102

Ser Gly Asp Ser Leu Gly Ile Leu Ala Arg Ser Pro Val Ser
1               5                   10

<210> SEQ ID NO 103
<211> LENGTH: 14
<212> TYPE: PRT
<213> ORGANISM: Artificial Sequence
<220> FEATURE:
<223> OTHER INFORMATION: LCDR1

<400> SEQUENCE: 103

Ser Gly Asp Ser Leu Gly Ile Leu Trp Leu Ser Pro Val Ser
1               5                   10

<210> SEQ ID NO 104
<211> LENGTH: 14
<212> TYPE: PRT
<213> ORGANISM: Artificial Sequence
<220> FEATURE:
<223> OTHER INFORMATION: LCDR1

<400> SEQUENCE: 104

Ser Gly Asp Ser Leu Gly Ile Ala Trp Ser Ser Ser Val Ser
1               5                   10

<210> SEQ ID NO 105
<211> LENGTH: 14
<212> TYPE: PRT
<213> ORGANISM: Artificial Sequence
<220> FEATURE:
<223> OTHER INFORMATION: LCDR1

<400> SEQUENCE: 105

Ser Gly Asp Ser Leu Gly Ile Cys Pro Leu Val Ser Val Ser
1               5                   10

<210> SEQ ID NO 106
<211> LENGTH: 14
<212> TYPE: PRT
<213> ORGANISM: Artificial Sequence
<220> FEATURE:
<223> OTHER INFORMATION: LCDR1

<400> SEQUENCE: 106

Ser Gly Asp Ser Leu Gly Ile Phe Leu Pro Gly Arg Val Ser
1               5                   10

<210> SEQ ID NO 107
<211> LENGTH: 14
<212> TYPE: PRT
<213> ORGANISM: Artificial Sequence
<220> FEATURE:
<223> OTHER INFORMATION: LCDR1

<400> SEQUENCE: 107

Ser Gly Asp Ser Leu Gly Ile Gly Trp Ser Gly Ser Val Ser
1               5                   10

<210> SEQ ID NO 108
<211> LENGTH: 14
```

```
<212> TYPE: PRT
<213> ORGANISM: Artificial Sequence
<220> FEATURE:
<223> OTHER INFORMATION: LCDR1

<400> SEQUENCE: 108

Ser Gly Asp Ser Leu Gly Ile Leu Gly Ser Gly Pro Val Ser
1               5                   10

<210> SEQ ID NO 109
<211> LENGTH: 14
<212> TYPE: PRT
<213> ORGANISM: Artificial Sequence
<220> FEATURE:
<223> OTHER INFORMATION: LCDR1

<400> SEQUENCE: 109

Ser Gly Asp Ser Leu Gly Ile Leu Arg Pro Ala Pro Val Ser
1               5                   10

<210> SEQ ID NO 110
<211> LENGTH: 14
<212> TYPE: PRT
<213> ORGANISM: Artificial Sequence
<220> FEATURE:
<223> OTHER INFORMATION: LCDR1

<400> SEQUENCE: 110

Ser Gly Asp Ser Leu Gly Ile Pro Ala Arg Ser Pro Val Ser
1               5                   10

<210> SEQ ID NO 111
<211> LENGTH: 14
<212> TYPE: PRT
<213> ORGANISM: Artificial Sequence
<220> FEATURE:
<223> OTHER INFORMATION: LCDR1

<400> SEQUENCE: 111

Ser Gly Asp Ser Leu Gly Ile Pro Ser Phe Ser Pro Val Ser
1               5                   10

<210> SEQ ID NO 112
<211> LENGTH: 14
<212> TYPE: PRT
<213> ORGANISM: Artificial Sequence
<220> FEATURE:
<223> OTHER INFORMATION: LCDR1

<400> SEQUENCE: 112

Ser Gly Asp Ser Leu Gly Ile Pro Trp Val Ser Gly Val Ser
1               5                   10

<210> SEQ ID NO 113
<211> LENGTH: 14
<212> TYPE: PRT
<213> ORGANISM: Artificial Sequence
<220> FEATURE:
<223> OTHER INFORMATION: LCDR1

<400> SEQUENCE: 113

Ser Gly Asp Ser Leu Gly Ile Arg Leu Phe Leu Pro Val Ser
1               5                   10

<210> SEQ ID NO 114
<211> LENGTH: 14
<212> TYPE: PRT
```

```
<213> ORGANISM: Artificial Sequence
<220> FEATURE:
<223> OTHER INFORMATION: LCDR1

<400> SEQUENCE: 114

Ser Gly Asp Ser Leu Gly Ile Ser Arg Ser Arg Tyr Val Ser
1               5                   10

<210> SEQ ID NO 115
<211> LENGTH: 14
<212> TYPE: PRT
<213> ORGANISM: Artificial Sequence
<220> FEATURE:
<223> OTHER INFORMATION: LCDR1

<400> SEQUENCE: 115

Ser Gly Asp Ser Leu Gly Ile Ser Arg Ser Thr Tyr Val Ser
1               5                   10

<210> SEQ ID NO 116
<211> LENGTH: 14
<212> TYPE: PRT
<213> ORGANISM: Artificial Sequence
<220> FEATURE:
<223> OTHER INFORMATION: LCDR1

<400> SEQUENCE: 116

Ser Gly Asp Ser Leu Gly Ile Thr Gln Ser Lys Tyr Val Ser
1               5                   10

<210> SEQ ID NO 117
<211> LENGTH: 14
<212> TYPE: PRT
<213> ORGANISM: Artificial Sequence
<220> FEATURE:
<223> OTHER INFORMATION: LCDR1

<400> SEQUENCE: 117

Ser Gly Asp Ser Leu Gly Ile Val Arg Ser Leu Gly Val Ser
1               5                   10

<210> SEQ ID NO 118
<211> LENGTH: 14
<212> TYPE: PRT
<213> ORGANISM: Artificial Sequence
<220> FEATURE:
<223> OTHER INFORMATION: LCDR1

<400> SEQUENCE: 118

Ser Gly Asp Ser Leu Gly Ile Trp Leu Cys Gly Pro Val Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: LCDR2

<400> SEQUENCE: 119

Ser Ala Ser Glu Arg Pro Ser
1               5

<210> SEQ ID NO 120
<211> LENGTH: 7
<212> TYPE: PRT
<213> ORGANISM: Artificial Sequence
```

```
<220> FEATURE:
<223> OTHER INFORMATION: LCDR2

<400> SEQUENCE: 120

Leu Pro Thr Ser Arg Pro Ser
1               5

<210> SEQ ID NO 121
<211> LENGTH: 7
<212> TYPE: PRT
<213> ORGANISM: Artificial Sequence
<220> FEATURE:
<223> OTHER INFORMATION: LCDR2

<400> SEQUENCE: 121

Gln Ser His Trp Arg Pro Ser
1               5

<210> SEQ ID NO 122
<211> LENGTH: 7
<212> TYPE: PRT
<213> ORGANISM: Artificial Sequence
<220> FEATURE:
<223> OTHER INFORMATION: LCDR2

<400> SEQUENCE: 122

Ser Asn Thr Thr Arg Pro Ser
1               5

<210> SEQ ID NO 123
<211> LENGTH: 7
<212> TYPE: PRT
<213> ORGANISM: Artificial Sequence
<220> FEATURE:
<223> OTHER INFORMATION: LCDR2

<400> SEQUENCE: 123

Ser Ala Glu Leu Arg Pro Ser
1               5

<210> SEQ ID NO 124
<211> LENGTH: 7
<212> TYPE: PRT
<213> ORGANISM: Artificial Sequence
<220> FEATURE:
<223> OTHER INFORMATION: LCDR2

<400> SEQUENCE: 124

Ser Tyr Arg Ser Arg Pro Ser
1               5

<210> SEQ ID NO 125
<211> LENGTH: 7
<212> TYPE: PRT
<213> ORGANISM: Artificial Sequence
<220> FEATURE:
<223> OTHER INFORMATION: LCDR2

<400> SEQUENCE: 125

Ser Ser Gln His Arg Pro Ser
1               5

<210> SEQ ID NO 126
<211> LENGTH: 7
<212> TYPE: PRT
<213> ORGANISM: Artificial Sequence
<220> FEATURE:
```

```
<223> OTHER INFORMATION: LCDR2

<400> SEQUENCE: 126

Ser His Gly Arg Arg Pro Ser
1               5

<210> SEQ ID NO 127
<211> LENGTH: 7
<212> TYPE: PRT
<213> ORGANISM: Artificial Sequence
<220> FEATURE:
<223> OTHER INFORMATION: LCDR2

<400> SEQUENCE: 127

Trp Ser Asn Asp Arg Pro Ser
1               5

<210> SEQ ID NO 128
<211> LENGTH: 7
<212> TYPE: PRT
<213> ORGANISM: Artificial Sequence
<220> FEATURE:
<223> OTHER INFORMATION: LCDR2

<400> SEQUENCE: 128

Phe Arg Val Ser Arg Pro Ser
1               5

<210> SEQ ID NO 129
<211> LENGTH: 7
<212> TYPE: PRT
<213> ORGANISM: Artificial Sequence
<220> FEATURE:
<223> OTHER INFORMATION: LCDR2

<400> SEQUENCE: 129

Ser Ala Tyr Leu Arg Pro Ser
1               5

<210> SEQ ID NO 130
<211> LENGTH: 7
<212> TYPE: PRT
<213> ORGANISM: Artificial Sequence
<220> FEATURE:
<223> OTHER INFORMATION: LCDR2

<400> SEQUENCE: 130

Asp Leu Met Ser Arg Pro Ser
1               5

<210> SEQ ID NO 131
<211> LENGTH: 7
<212> TYPE: PRT
<213> ORGANISM: Artificial Sequence
<220> FEATURE:
<223> OTHER INFORMATION: LCDR2

<400> SEQUENCE: 131

Leu Lys Ser Gln Arg Pro Ser
1               5

<210> SEQ ID NO 132
<211> LENGTH: 7
<212> TYPE: PRT
<213> ORGANISM: Artificial Sequence
<220> FEATURE:
<223> OTHER INFORMATION: LCDR2
```

```
<400> SEQUENCE: 132

Leu Pro Thr Phe Arg Pro Ser
1               5

<210> SEQ ID NO 133
<211> LENGTH: 7
<212> TYPE: PRT
<213> ORGANISM: Artificial Sequence
<220> FEATURE:
<223> OTHER INFORMATION: LCDR2

<400> SEQUENCE: 133

Ala Asn Glu Leu Arg Pro Ser
1               5

<210> SEQ ID NO 134
<211> LENGTH: 7
<212> TYPE: PRT
<213> ORGANISM: Artificial Sequence
<220> FEATURE:
<223> OTHER INFORMATION: LCDR2

<400> SEQUENCE: 134

Pro Arg Thr Pro Arg Pro Ser
1               5

<210> SEQ ID NO 135
<211> LENGTH: 7
<212> TYPE: PRT
<213> ORGANISM: Artificial Sequence
<220> FEATURE:
<223> OTHER INFORMATION: LCDR2

<400> SEQUENCE: 135

Pro Asn Ala Arg Arg Pro Ser
1               5

<210> SEQ ID NO 136
<211> LENGTH: 7
<212> TYPE: PRT
<213> ORGANISM: Artificial Sequence
<220> FEATURE:
<223> OTHER INFORMATION: LCDR2

<400> SEQUENCE: 136

Pro Ser Asp His Arg Pro Ser
1               5

<210> SEQ ID NO 137
<211> LENGTH: 7
<212> TYPE: PRT
<213> ORGANISM: Artificial Sequence
<220> FEATURE:
<223> OTHER INFORMATION: LCDR2

<400> SEQUENCE: 137

Ala Ser Gln Ser Arg Pro Ser
1               5

<210> SEQ ID NO 138
<211> LENGTH: 7
<212> TYPE: PRT
<213> ORGANISM: Artificial Sequence
<220> FEATURE:
<223> OTHER INFORMATION: LCDR2
```

<400> SEQUENCE: 138

Ser Ala Glu Leu Arg Pro Ser
1               5

<210> SEQ ID NO 139
<211> LENGTH: 7
<212> TYPE: PRT
<213> ORGANISM: Artificial Sequence
<220> FEATURE:
<223> OTHER INFORMATION: LCDR2

<400> SEQUENCE: 139

Ser Ala Lys Leu Arg Pro Ser
1               5

<210> SEQ ID NO 140
<211> LENGTH: 7
<212> TYPE: PRT
<213> ORGANISM: Artificial Sequence
<220> FEATURE:
<223> OTHER INFORMATION: LCDR2

<400> SEQUENCE: 140

Ser Ala Glu Leu Arg Pro Ser
1               5

<210> SEQ ID NO 141
<211> LENGTH: 7
<212> TYPE: PRT
<213> ORGANISM: Artificial Sequence
<220> FEATURE:
<223> OTHER INFORMATION: LCDR2

<400> SEQUENCE: 141

Leu Asn Gly Arg Arg Pro Ser
1               5

<210> SEQ ID NO 142
<211> LENGTH: 7
<212> TYPE: PRT
<213> ORGANISM: Artificial Sequence
<220> FEATURE:
<223> OTHER INFORMATION: LCDR2

<400> SEQUENCE: 142

Leu Pro Arg Ser Arg Pro Ser
1               5

<210> SEQ ID NO 143
<211> LENGTH: 14
<212> TYPE: PRT
<213> ORGANISM: Artificial Sequence
<220> FEATURE:
<223> OTHER INFORMATION: A11 LCDR1

<400> SEQUENCE: 143

Ser Gly Asp Ser Leu Gly Ile Gly Ser Asn Asn Tyr Val Ser
1               5                   10

<210> SEQ ID NO 144
<211> LENGTH: 7
<212> TYPE: PRT
<213> ORGANISM: Artificial Sequence
<220> FEATURE:
<223> OTHER INFORMATION: A11 LCDR2

<400> SEQUENCE: 144

Asp Asp Asn Lys Arg Pro Ser
1               5

<210> SEQ ID NO 145
<211> LENGTH: 109
<212> TYPE: PRT
<213> ORGANISM: Artificial Sequence
<220> FEATURE:
<223> OTHER INFORMATION: VL 109

<400> SEQUENCE: 145

Gln Ser Ala Leu Thr Gln Pro Ala Ser Val Ser Gly Ser Pro Gly Gln
1               5                   10                  15

Ser Ile Thr Ile Ser Cys Ser Gly Asp Ser Leu Gly Ile Phe Arg Ser
            20                  25                  30

Gly Met Val Ser Trp Tyr Gln Gln His Pro Gly Lys Ala Pro Lys Leu
        35                  40                  45

Met Ile Tyr Leu Pro Thr Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ser Trp Asp Gly Arg
                85                  90                  95

Gln Pro Val Phe Gly Gly Gly Thr Lys Leu Thr Val Leu
            100                 105

<210> SEQ ID NO 146
<211> LENGTH: 241
<212> TYPE: PRT
<213> ORGANISM: Artificial Sequence
<220> FEATURE:
<223> OTHER INFORMATION: A11 variant

<400> SEQUENCE: 146

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Met Ser Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Ser Gln Ser Ala Leu Thr Gln Pro Ala Ser Val Ser Gly
    130                 135                 140

Ser Pro Gly Gln Ser Ile Thr Ile Ser Cys Ser Gly Asp Ser Leu Gly
145                 150                 155                 160

Ile Gly Ser Asn Asn Tyr Val Ser Trp Tyr Gln Gln His Pro Gly Lys
                165                 170                 175

Ala Pro Lys Leu Met Ile Tyr Asp Asp Asn Lys Arg Pro Ser Gly Val

|  | 180 | 185 | 190 |
| --- | --- | --- | --- |

Ser Asn Arg Phe Ser Gly Ser Lys Ser Gly Asn Thr Ala Ser Leu Thr
    195                 200                 205

Ile Ser Gly Leu Gln Ala Glu Asp Glu Ala Asp Tyr Tyr Cys Gln Ser
    210                 215                 220

Trp Asp Gly Arg Gln Pro Val Phe Gly Gly Gly Thr Lys Leu Thr Val
225                 230                 235                 240

Leu

<210> SEQ ID NO 147
<211> LENGTH: 327
<212> TYPE: DNA
<213> ORGANISM: Artificial Sequence
<220> FEATURE:
<223> OTHER INFORMATION: coding for VL 109

<400> SEQUENCE: 147

```
cagtctgccc tgactcagcc tgcctccgtg tctgggtctc ctggccagtc gatcaccatc      60
tcctgcagcg gtgatagcct gggtattttt cggtctggta tggtctcctg gtaccaacag     120
cacccaggca agcccccaa actcatgatt tatcttccta cgtcgcgccc ctcaggcgtt      180
tctaaccggt tctctggctc caagtctggc aacacggcct ccctgaccat ctctggtctc     240
caggctgagg acgaggctga ttattactgc cagtcatggg atgggcggca gccggtcttc     300
ggcggtggca ctaaactgac tgtgctg                                         327
```